(12) United States Patent
Raz et al.

(10) Patent No.: US 10,941,445 B2
(45) Date of Patent: Mar. 9, 2021

(54) UNIVERSAL HAIRPIN PRIMERS

(71) Applicant: Bio-Rad Laboratories, Inc., Hercules, CA (US)

(72) Inventors: Tal Raz, Brookline, MA (US); Pascaline Mary, Cambridge, MA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 155 days.

(21) Appl. No.: 15/926,341

(22) Filed: Mar. 20, 2018

(65) Prior Publication Data
US 2018/0274029 A1 Sep. 27, 2018

Related U.S. Application Data

(60) Provisional application No. 62/476,108, filed on Mar. 24, 2017.

(51) Int. Cl.
| | |
|---|---|
| *C12Q 1/6876* | (2018.01) |
| *C12Q 1/6869* | (2018.01) |
| *C12Q 1/6848* | (2018.01) |
| *C12Q 1/6806* | (2018.01) |
| *C12Q 1/682* | (2018.01) |

(52) U.S. Cl.
CPC .......... *C12Q 1/6876* (2013.01); *C12Q 1/682* (2013.01); *C12Q 1/6806* (2013.01); *C12Q 1/6848* (2013.01); *C12Q 1/6869* (2013.01)

(58) Field of Classification Search
CPC .. C12Q 1/6876; C12Q 1/6869; C12Q 1/6848; C12Q 1/682; C12Q 1/6806; C12Q 1/686
See application file for complete search history.

(56) References Cited

U.S. PATENT DOCUMENTS

| | | | |
|---|---|---|---|
| 6,117,635 A | 9/2000 | Nazarenko et al. | |
| 6,964,847 B1* | 11/2005 | Englert | C07H 21/04 382/129 |
| 7,097,980 B2 | 8/2006 | Barany et al. | |
| 2014/0024033 A1 | 1/2014 | Jia et al. | |
| 2014/0242586 A1 | 8/2014 | Whitman et al. | |
| 2015/0344948 A1* | 12/2015 | Sanders | C12Q 1/6869 506/16 |
| 2016/0076082 A1 | 3/2016 | Raz et al. | |
| 2016/0355880 A1 | 12/2016 | Gormley et al. | |
| 2018/0010176 A1* | 1/2018 | Patel | C12Q 1/6806 |

FOREIGN PATENT DOCUMENTS

| | | |
|---|---|---|
| WO | 2014/062717 A1 | 4/2014 |
| WO | 2016/138080 A1 | 9/2016 |

OTHER PUBLICATIONS

Kaboev et al. Nucleic Acids Research 2000; 28: e94 (Year: 2000).*

(Continued)

*Primary Examiner* — Angela M. Bertagna
(74) *Attorney, Agent, or Firm* — Kilpatrick Townsend and Stockton LLP

(57) ABSTRACT

The present invention relates to methods of target nucleic acid amplification and uses thereof in methods of sequencing, or other down-stream applications such a genotyping or cloning. More specifically, the methods relate to methods of target nucleic acid amplification through the use of a universal hairpin primer.

12 Claims, 4 Drawing Sheets

Specification includes a Sequence Listing.

(56) References Cited

OTHER PUBLICATIONS

Faltin, B. et al.; "Current Methods for Fluorescence-Based Universal Sequence-Dependent Detection of Nucleic Acids in Homogenous Assays and Clinical Applications"; *Clinical Chemistry*; vol. 59, No. 11; 2013; pp. 1567-1582.

Nazarenko, I.A. et al.; "A closed tube format for amplification and detection of DNA based on energy transfer"; *Nucleic Acids Research*; vol. 25, No. 12; 1997; pp. 2516-2521.

Nuovo, G.J. et al.; "In Situ Amplification Using Universal Energy Transfer-labeled Primers"; *The Journal of Histochemistry & Cytochemistry*; vol. 47, No. 3; 1999; pp. 273-279.

Singh, V.K. et al.; "The Effect of Hairpin Structure on PCR Amplification Efficiency"; *Molecular Biology Today*; vol. 1, No. 3; 2000; pp. 67-69.

Stahlberg, A. et al.; "Simple, multiplexed, PCR-based barcoding of DNA enables sensitive mutation detection in liquid biopsies using sequencing"; *Nucleic Acids Research*; Apr. 7, 2016; pp. 1-7.

"(GX-30-S7901 100rct, GX-30-S7905 1000 rct, GX-30-S7903 10.000 rct Amplifluor™ Universal Detection System"; downloaded from www.gene-quantification.com/amplifluor-universal.pdf on May 17, 2017; 4 pages.

International Search Report and Written Opinion for PCT/US2018/023305 dated Aug. 1, 2018; 14 pages.

\* cited by examiner

UNIVERSAL HAIRPIN PRIMERS

CROSS-REFERENCE TO RELATED APPLICATIONS

This application claims priority to U.S. Provisional Application No. 62/476,108, filed Mar. 24, 2017, which is incorporated in its entirety herein for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 097505-113810US-1079935_SequenceListing.txt, created on Mar. 19, 2018, 1,028 bytes, machine format IBM-PC, MS-Windows operating system, is hereby incorporated by reference in its entirety for all purposes.

BACKGROUND OF THE INVENTION

There are numerous methods for the amplification of a target nucleic acid of interest. Some of these methods, such as PCR and its derivatives, are well-used throughout the molecular biology industry. PCR is a sensitive and specific assay allowing for the detection of minute quantities of a target nucleotide sequence in large amounts of non-target nucleic acid material. For example, PCR based methods for the detection of low amounts of DNA, such as cell-free DNA from plasma samples of pregnant women to screen for fetal aneuploidy or detection of circulating tumor DNA (ctDNA) in blood samples of cancer patients are known, see for example, US Patent Application Nos.: 20150147815, 20150087535, and 20160138112, and U.S. Pat. Nos. 9,334,541, and 9,499,870, the disclosures of which are incorporated herein by reference.

The continued expansion of PCR principles has led many companies to dedicate significant resources to streamlining nucleic acid library preparation procedures and amplification processes, for example, reactions performed in aqueous solutions, microdroplets, emulsions, and solid-phase based nucleic acid amplifications (e.g., Illumina Inc., Ion Torrent, 454 Life Sciences, and Pacific Biosciences). Further refinement of nucleic acid amplification methods has led to the development of multiplex nucleic acid amplification reactions allowing for the amplification of hundreds or thousands of nucleic acid targets in a single reaction mixture, see for example, US Patent Application 20160369333 and U.S. Pat. Nos. 8,673,560, and 8,728,728, the disclosures of which are incorporated herein by reference. Accordingly, the design of primers and their function in nucleic acid amplification reactions is important to prevent and/or reduce the likelihood of mis-priming and/or failed priming events, the development of multiplex nucleic acid amplification reactions, and the need for less optimization of individual primer concentrations as the parameters of nucleic acid amplification reactions become more harmonized.

Some parameters for primer design of nucleic acid amplification reactions are well documented, such as percent GC content, primer length, annealing and melting temperatures, 5' end stability and 3' end specificity (Dieffenbach et al., In: PCR Methods and Applications, Cold Spring Harbor Laboratory, 3: S30-S37 (1993)). Another consideration of primer design is the presence of secondary structures, such as hairpins (stem loops) or primer dimers. Hairpins can greatly reduce the efficiency of PCR reactions by limiting the primers availability for priming and its ability to bind to a target nucleic acid of interest. These secondary structures lead to failed, disproportionate, or inefficient nucleic acid amplification because of the presence of complementary nucleic acid sequences within the secondary structure of the primer. Several algorithms exist that allow users to input potential primer designs to determine the presence of secondary structures (e.g., NCBI BLAST-Primer software, Primer3Plus software). Generally, primers having significant secondary structure are disregarded in favor of comparable primers lacking secondary structures to maximize efficiency of the nucleic acid amplification reaction (see, for example, Singh et al., Mol Biol., 1(3): 67-69 (2000)). Here, we provide improved methods, kits and reaction mixtures for the amplification of nucleic acids.

BRIEF SUMMARY OF THE INVENTION

Provided herein are methods, kits, and reaction mixtures, for nucleic acid amplification. The methods comprise using a first target primer pair comprising one or two target-specific hairpin primers having (i) a 3' single-stranded target-specific region at or below a Tm temperature, (ii) a 5' region that forms a hairpin below a Tm temperature and that does not form the hairpin above the Tm temperature, and a universal primer pair comprising one or two hairpin primers having said 5' region and lacking a single-stranded 3' end as determined below the Tm temperature. In some embodiments, the 3' single-stranded target-specific region of a first target primer pair is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin.

In some embodiments, the methods comprise (1) mixing a first target nucleic acid with (a) a first target primer pair, the first target primer pair comprising one or two first target-specific hairpin primers, the hairpin primers having (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence, and (b) a universal primer pair comprising one or two universal hairpin primers (i) having said 5' region, and (ii) lacking a single-stranded 3' end as determined below the Tm temperature; (2) annealing the 3' single-stranded target-specific region of at least one first target-specific hairpin primer from the first target primer pair to the first target nucleic acid at a temperature at or below the Tm temperature and extending the target-specific hairpin primer with a polymerase in a template dependent manner to form a first amplicon comprising one or two universal adaptor sequences, (3) denaturing the first amplicon into two nucleic acid strands; (4) annealing the one or two universal hairpin primers to the universal adaptor sequence of one of the strands of the first amplicon at a temperature above the Tm temperature of the hairpin, (5) extending the one or two universal hairpin primers with a polymerase in a template dependent manner to form a second amplicon, thereby amplifying the first target nucleic acid. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin. In some embodiments, the methods further comprise sequencing or purifying the second amplicon. In one embodiment, purifying the second amplicon can include purifying the second amplicon from the non-amplified nucleic acid material. In one embodiment, purifying the second amplicon can include isolating or compartmentalizing of the second amplicon of a first target nucleic acid from the second amplicon of a second target nucleic acid. In some embodiments, the sequencing can include massively parallel next generation sequencing (NGS). In some embodiments, the methods of nucleic acid amplification disclosed herein comprise asymmetric or nested PCR. In some embodiments, the methods disclosed herein comprise real-time analysis of nucleic acid amplification. In some embodiments, the methods disclosed herein comprise bridge PCR or cluster amplification. In one embodiment, the target nucleic acid amplification is performed in a microdroplet. In another embodiment, the target nucleic acid is dilute so that single genomic targets, on average, from the target nucleic acid are partitioned into individual microdroplets. In some embodiments, the target nucleic acid, first target primer pair and universal primer pair are partitioned into a microdroplet.

In some embodiments, the first target primer pair of the method described in the preceding paragraph comprises two target-specific hairpin primers. In some embodiments, the method comprises repeating steps (2) and (3) multiple times. In one embodiment, steps (2) and (3) are repeated 5, 6, 7, 8, 9, 10, 11, 12, 13, 14, or 15 times. In some embodiments, steps (2) and (3) are repeated from 5 to 15 cycles and steps (4) and (5) are repeated from 5 to 30 cycles. In one embodiment, steps (4) and (5) are repeated 5, 6, 7, 8, 9, 10, 11, 12, 13, 14, 15, 16, 17, 18, 19, 20, 21, 22, 23, 24, 25, 26, 27, 28, 29, or 30 times. In some embodiments, the first target primer pair is exhausted prior to step (4). In some embodiments, the first target primer pair is not linked to or includes a label. In some embodiments, the universal primer pair of the method described in the preceding paragraph comprises two universal hairpin primers. In some embodiments, the universal primer pair of step (1) is present in a quantity greater than the quantity of the first target primer pair. In some embodiments, the universal primer pair of step (1) comprises at least one universal hairpin primer linked to a label such that the label is incorporated into the second amplicon during amplification. In one embodiment, the label is at the 5' end of the universal hairpin primer. In one embodiment, the label is a fluorophore. In one embodiment, the label comprises a FRET donor and FRET acceptor molecule.

In some embodiments, the methods comprise a first target-specific hairpin primer having a 5' region that forms a hairpin below a Tm temperature (melting temperature) and that does not form the hairpin above the Tm temperature, and a 3' target specific region. In one embodiment, the Tm temperature of the first target-specific hairpin primer minus the 3' target specific region is within 5° C. of the melting temperature of universal hairpin primer. In one embodiment, the Tm temperature of the first target-specific hairpin primer minus the 3' target specific region is within 3° C. of the melting temperature of the universal hairpin primer. In one embodiment, the Tm temperature of the first target-specific hairpin primer minus the 3' target specific region is within 1° C. of the melting temperature of the universal hairpin primer. In another embodiment, the Tm temperature of the first target-specific hairpin primer minus the 3' target specific region is 2° C. lower than the melting temperature of the universal hairpin primer. In another embodiment, the Tm temperature of the first target-specific hairpin primer minus the 3' target specific region is at least 2° C. lower than the melting temperature of the universal hairpin primer. In yet another embodiment, the Tm temperature of the first target-specific hairpin primer minus the 3' target specific region is 2° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., or more than 3.5° C., lower than the melting temperature of the universal hairpin primer.

In some embodiments, the method of step (1) further comprises mixing a second target primer pair comprising one or two second target-specific hairpin primers, the second target-specific hairpin primers having (i) a 3' single-stranded target-specific region different from the 3' single-stranded target-specific regions of the first target-specific hairpin primers and (ii) said 5' region; step (2) comprises annealing at least one second target-specific hairpin primer from the second target primer pair to a second target nucleic acid at a temperature at or below the Tm temperature and extending the second target-specific hairpin primer with the polymerase in a template dependent manner to form a first extension product comprising one or two universal adaptor sequences, step (3) comprises denaturing the first extension product into two nucleic acid strands; step (4) comprises annealing the one or two universal hairpin primers to a universal adaptor sequence of one of the strands of the first extension product at a temperature above the Tm temperature, and step (5) comprises extending the one or two universal hairpin primers with a polymerase in a template dependent manner to form a second extension product, thereby amplifying the second target nucleic acid. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin. In one embodiment, the second target-specific primer pair comprises two target-specific hairpin primers. In some embodiments, the one or two universal hairpin primers comprise two universal hairpin primers. In some embodiments, the method further comprises sequencing or purifying the second extension product. In some embodiments, the methods of nucleic acid amplification disclosed herein comprise asymmetric or nested PCR. In some embodiments, the methods disclosed herein comprise real-time analysis of nucleic acid amplification In some embodiments, the methods disclosed herein comprise mixing three or more target primer pairs to amplify three or more target nucleic acids. In one embodiment, the three or more target primer pairs each comprise two target-specific hairpin primers for different ones of the three or more target nucleic acids having a 3' single-stranded target-specific region at or below a Tm temperature and a 5' region that forms a hairpin below a Tm temperature and that does not form a hairpin above the Tm temperature, wherein the 5' region comprises a universal adaptor sequence, and wherein the 3' single-stranded target-specific region is different among the three or more target primer pairs so as to amplify a different target nucleic acid among the three or more target nucleic acids. In some embodiments, each target primer pair is designed such that the two target-specific hairpin primers amplify a distinct target nucleic acid (e.g., a single loci) as compared to other target primer pairs present in the amplification. In some embodiments, each of the target primer pairs comprises one forward (upstream) target-specific primer and one reverse (downstream) target-specific primer for each target nucleic acid to be amplified. In some embodiments, the method comprises mixing up to 50 different target primer pairs to amplify up to 50 different target nucleic acids. In one embodiment, the method comprises mixing 50 target primer pairs comprising 50 different forward target primers having a 3' single-stranded region and a 5' region that forms a hairpin below a Tm temperature and that does not form the hairpin above the Tm temperature, and 50 different reverse target primers having a 3' single-stranded region and a 5' region that forms a hairpin below a Tm temperature and that does not form the hairpin above the Tm temperature, thereby allowing for the amplification of 50 different target nucleic acids. In another embodiment, the method comprises mixing 100 target primer pairs comprising 100 forward target primers each having a 3' single-stranded region distinct from the 3' single-stranded region of another forward target primer, and 100 reverse target primers each having a 3' single-stranded region distinct from the 3' single-stranded region of another reverse target primer, thereby allowing for the amplification of 100 distinct target nucleic acids. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin.

In another aspect, the invention provides a kit that comprises (a) a first target primer pair, the first target primer pair comprising one or two first target-specific hairpin primers, the first target-specific hairpin primers having (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence, and (b) a universal primer pair comprising one or two universal hairpin primers (i) having said 5' region, and (ii) lacking a single-stranded 3' end as determined below the hairpin Tm temperature. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin. In some embodiments, the first target primer pair of the kit comprises two target-specific hairpin primers. In some embodiments, the first target primer pair of the kit is not linked to a label. In some embodiments, the universal primer pair of the kit comprises two universal hairpin primers. In one embodiment, the universal primer pair is present in a quantity greater than the quantity of the first target primer pair. In another embodiment, the universal hairpin primer of the universal primer pair is linked to a label. In one embodiment, the label is a fluorophore. In another embodiment, the label comprises a FRET donor and FRET acceptor molecule. In some embodiments, the kit further comprises a polymerase, a buffer and dNTPs. In some embodiments, the kit includes dNTPs for all anticipated triphosphate incorporations (e.g., dATP, dTTP, dGTP, dCTP, and where appropriate, dUTP).

In one embodiment, the kit further comprises a second target primer pair comprising one or two second target-specific hairpin primers, the second hairpin primers having (i) a 3' single-stranded target-specific region different from the 3' single-stranded target-specific regions of the first target-specific hairpin primers and (ii) said 5' region. In one embodiment, the second target primer pair comprises two target-specific hairpin primers. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin.

In another embodiment, the kit comprises three or more target primer pairs, where each target primer pair comprises two target-specific hairpin primers to amplify one of the three or more target nucleic acids. In some embodiments, each of the target primer pairs comprises one forward (upstream) target-specific hairpin primer and one reverse (downstream) target-specific hairpin primer having (i) a 3' single-stranded target-specific region different from the 3' single-stranded target-specific region of another target primer pair in the kit and (ii) said 5' region, for each target nucleic acid to be amplified. In some embodiments, the kit comprises up to 50 different target primer pairs to amplify up to 50 different target nucleic acids. In one embodiment, the kit comprises 100 target primer pairs comprising 100 forward target primers having a 3' single-stranded region distinct from the 3' single-stranded region of another forward target primer in the kit, and a 5' region that forms a hairpin below a Tm temperature and that does not form the hairpin above the Tm temperature, and 100 reverse target primers having a 3' single-stranded region distinct from the 3' single-stranded region of another reverse target primer in the kit, and a 5' region that forms a hairpin below a Tm temperature and that does not form the hairpin above the Tm temperature, thereby allowing for the amplification of 100 different target nucleic acids. In some embodiments, the kit further comprises between 1 and 10, 1 and 20, 1 and 30, 1 and 40, or 1 and 50, additional target primer pairs, wherein the additional target primer pairs comprise one or two target-specific hairpin primers having (i) a 3' single-stranded target-specific region different from the 3' single-stranded target-specific region of any other target-specific hairpin primers in the kit and (ii) said 5' region.

In some embodiments, the kit further comprises one or more additional reagents to stabilize or promote target nucleic acid amplification. In some embodiments, the reagents stabilize proteins such as polymerases during storage, prior to amplification, and/or during the amplification process. In one embodiment, the one or more additional reagents include non-ionic detergents such as polyethylene glycol (PEG), Tween 20, Triton X-100, or ethoxylated alky phenol (NP-40) (see for example, but not limited to, U.S. Pat. No. 6,127,155). In another embodiment, the one or more additional reagents to promote nucleic acid amplification include zwitterionic detergents (see for example, but not limited to, U.S. Pat. No. 797,282; US Patent Application No.: 20100099150; European Patent 2069487B1, each incorporated herein by reference). In some embodiments, the one or more additional reagents to stabilize or promote target nucleic acid amplification include reagents that stabilize polymerases used in the target nucleic acid amplification (see for example, but not limited to, US Patent Application 20100159528, incorporated herein by reference, discloses the use of anionic detergents to stabilize the activity of thermostable DNA polymerases).

In a further aspect, the invention provides a reaction mixture comprising (1) a sample having one or more target nucleic acids, and (2) a first target primer pair, the first target primer pair comprising one or two first target-specific hairpin primers, the hairpin primers having (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence, and a universal primer pair comprising one or two universal hairpin primers (i) having said 5' region, and (ii) lacking a single-stranded 3' end as determined below the Tm temperature. In one embodiment, the first target primer pair comprises two target-specific hairpin primers. In one embodiment, the first target primer pair is not linked to a label. In one embodiment, the universal primer pair comprises two universal hairpin primers. In another embodiment, the universal primer pair is present in a quantity greater than the quantity of the first target primer pair. In yet another embodiment, one universal hairpin primer of the universal primer pair is linked to a label. In one embodiment, the label is a fluorophore. In another embodiment, the label comprises a FRET donor and FRET acceptor molecule. In some embodiments, the reaction mixture includes dNTPs for all anticipated triphosphate incorporations (e.g., dATP, dTTP, dGTP, dCTP, and where appropriate, dUTP). In one embodiment, the reaction mixture is partitioned into microdroplets. In some embodiments, the microdroplets are emulsions. In some embodiments, the reaction mixture further comprises between 1 and 10, 1 and 20, 1 and 30, 1 and 40, or 1 and 50, additional target primer pairs, wherein the additional target primer pairs comprise one or two target-specific hairpin primers having (i) a 3' single-stranded target-specific region that is different from the 3' single-stranded target-specific region of any other target-specific hairpin primer in the reaction mixture and (ii) said 5' region.

In one embodiment, the reaction mixture further comprises a second target primer pair comprising one or two second target-specific hairpin primers, the second hairpin primers having (i) a 3' single-stranded target-specific region different from the 3' single-stranded target-specific regions of the first target-specific hairpin primers and (ii) said 5' region. In one embodiment, the second target primer pair comprises two target-specific hairpin primers.

In another embodiment, the reaction mixture comprises three or more target primer pairs, where each target primer pair comprises two target-specific hairpin primers to amplify one of the three or more target nucleic acids. In some embodiments, each of the target primer pairs comprises one forward (upstream) target-specific primer and one reverse (downstream) target-specific primer having (i) a 3' single-stranded target-specific region different from the 3' single-stranded target-specific region of another target primer pair and (ii) said 5' region for each target nucleic acid to be amplified. In some embodiments, the reaction mixture comprises up to 50 different target primer pairs to amplify up to 50 different target nucleic acids. In one embodiment, the reaction mixture comprises 100 target primer pairs comprising 100 different forward target primers having a 3' single-stranded region distinct from the 3' single-stranded region of another forward target primer, and a 5' region that forms a hairpin below a Tm temperature and that does not form the hairpin above the Tm temperature, and 100 different reverse target primers having a 3' single-stranded region distinct from the 3' single-stranded region of another reverse target primer, and a 5' region that forms a hairpin below a Tm temperature and that does not form the hairpin above the Tm temperature, thereby allowing for the amplification of 100 different target nucleic acids.

In one embodiment, the reaction mixture further comprises amplification reagents for amplifying at least one of the one or more target nucleic acids present in a sample. In some embodiments, the sample is diluted so that single genomic targets, on average, from the sample are partitioned into individual microdroplets. In another embodiment, the sample is diluted so that between 0 and 3 genomic targets, on average, from the sample are partitioned into individual microdroplets. In some embodiments, the amplification reagents include a polymerase, a buffer and dNTPs. In another embodiment, the reaction mixture further comprises one or more reagents to stabilize or promote amplification of the target nucleic acids. In some embodiments, the reagents stabilize proteins such as polymerases during storage, prior to amplification, and/or during the amplification process. In one embodiment, the one or more additional reagents include non-ionic detergents such as polyethylene glycol (PEG), Tween 20, Triton X-100, or ethoxylated alky phenol (NP-40) (see for example, but not limited to, U.S. Pat. No. 6,127,155). In another embodiment, the one or more additional reagents to promote nucleic acid amplification include zwitterionic detergents (see for example, but not limited to, U.S. Pat. No. 797,282; US Patent Application No.: 20100099150; European Patent 2069487B1, each incorporated herein by reference). In some embodiments, the one or more additional reagents to stabilize or promote target nucleic acid amplification include reagents that stabilize polymerases used in the target nucleic acid amplification (see for example, but not limited to, US Patent Application 20100159528, incorporated herein by reference, discloses the use of anionic detergents to stabilize the activity of thermostable DNA polymerases).

In some embodiments, the reaction mixture disclosed herein can be used for asymmetric or nested PCR. In some embodiments, the reaction mixture disclosed herein can be used for real-time analysis of nucleic acid amplification. In some embodiments, the target nucleic acid amplified in the reaction mixture can be sequenced, purified, or utilized in one or more downstream applications such as cloning, genotyping, detection and/or identification of genetic variants, detection and/or identification of pathogens, or detection and/or identification of foreign nucleic acids in the reaction mixture.

BRIEF DESCRIPTION OF THE DRAWINGS

FIG. 1 demonstrates four sets of target-specific primer pairs, designed to amplify four different target nucleic acids in a sample or reaction (Target 1, Target 2, Target 3, and Target 4). The target-specific primer pairs (TSPPs) are present in the amplification reaction mixture in low abundance such that during the amplification reaction, the TSPPs are exhausted. The primer design strategy also includes a universal primer pair that lacks a 3' single-stranded target-specific region and is therefore not capable of acting as a priming binding site during the first round of amplification. In some embodiments, the universal primer pair is present in the nucleic acid amplification reaction mixture in high abundance as compared to the TSPPs.

FIG. 2 demonstrates the first amplification reaction using a first (low) annealing temperature, thereby allowing the TSPPs to anneal to a complementary sequence present in the target nucleic acids of the reaction mixture (e.g., shown here as the annealing of TSPP Target 4 to a complementary target nucleic acid in the reaction mixture); and extension of the TSPP, for example in a template dependent manner, to form a first amplification product (first amplicon). The three remaining TSPPs (shown here as Target 1-3) and the universal primer pair of FIG. 2 do not anneal to target nucleic acids present in the reaction mixture because of a lack of complementarity between the target-specific primer pairs and the universal primer pair with the target nucleic acids. Additionally, the first (low) annealing temperature is below the melting temperature of the hairpin structure of the universal primer pair, such that the hairpin structure is maintained during the first (low) annealing step.

FIG. 3 demonstrates a second (high) annealing temperature applied to the reaction mixture after formation of the first amplicon. The high annealing temperature allows the universal primer pair present in the reaction mixture to transition from a hairpin to linear configuration, thereby facilitating hybridization of the universal primer pair to a complementary sequence present in the universal adaptor sequence of the first amplicon. In one embodiment, the second (high) annealing temperature is above the Tm temperature of the 5' region of the TSPP but below the Tm temperature of the universal hairpin primer.

FIG. 4 demonstrates application of the high annealing temperature as discussed in the preceding paragraph, on the universal primer pair and subsequent extension, for example in a template dependent manner, to form second amplicons. The linear universal primer pair contains a nucleotide sequence that is complementary to the universal adaptor sequence present in the TSPPs and therefore can act as a priming binding site. Once annealed to the universal adaptor sequence present in the first amplicon, the universal primer pair can be extended, for example in a template dependent manner, to form second amplicons. The second amplicons can be used in any appropriate downstream application such as nucleic acid sequencing, cloning, or genotyping.

DETAILED DESCRIPTION OF THE INVENTION

Figure 1:
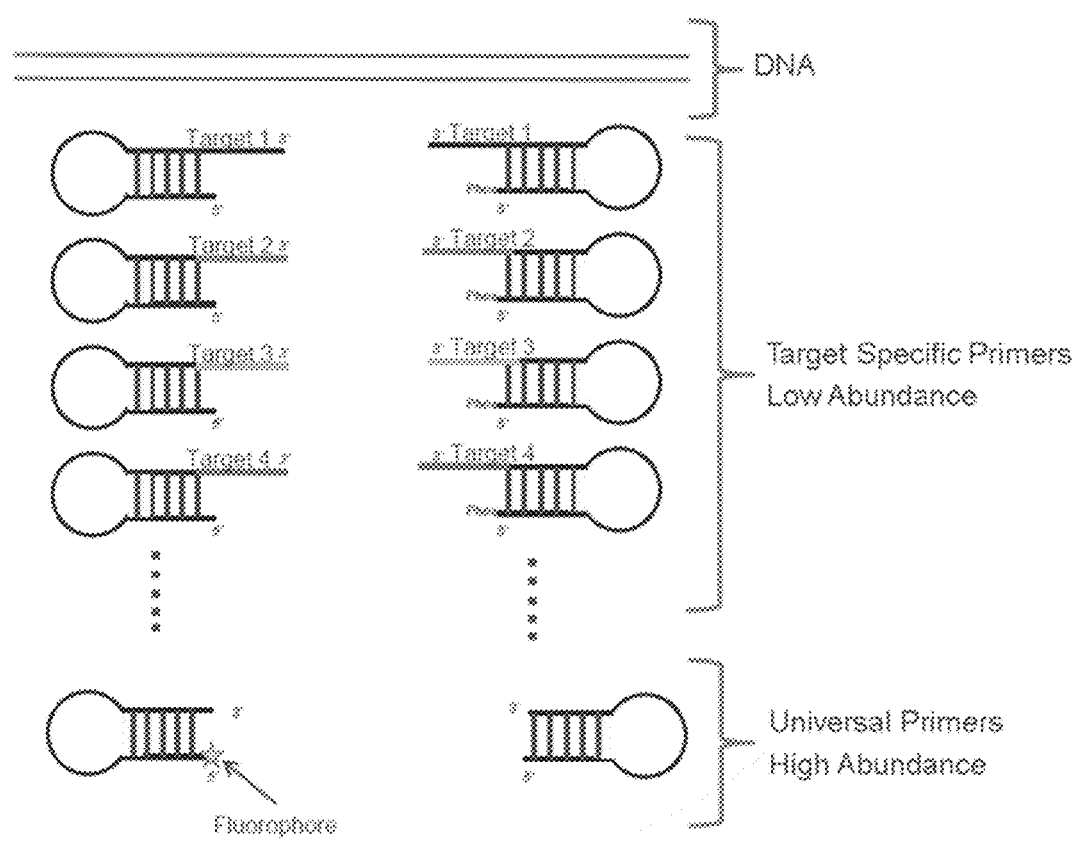
FIG. 1 is a schematic outlining an exemplary primer design strategy of the instant application.

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Generally, the nomenclature used herein and the laboratory procedures in cell culture, molecular biology, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference), which are provided throughout this document.

Terminology

As used herein, the terms "a," "an," and "the" are defined to mean one or more and include the plural unless the context is inappropriate. Ranges may be expressed herein as from "about" one specified value, and/or to "about" another specified value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. When such a range is expressed, another embodiment includes from the one specific value and/or to the other specified value. Similarly, when values are expressed as approximations, by use of the antecedent "about," it will be understood that the specified value forms another embodiment. It will be further understood that the endpoints of each of the ranges are included with the range.

The word "or" as used herein means any one member of a particular list and also includes any combination of members of that list.

As used herein, the term "amplification" or "amplifying" refers to any in vitro means for multiplying the copies of a target nucleic acid. Such methods include, but are not limited to, polymerase chain reaction (PCR), DNA ligase chain reaction (LCR) (see U.S. Pat. Nos. 4,683,195 and 4,683,202); PCR Protocols: A Guide to Methods and Applications (Innis et al., eds, 1990)), RT-PCR, QBeta RNA replicase, and RNA transcription-based (such as TAS) amplification reactions as well as others known to those of skill in the art. Asymmetric PCR, nested PCR, bridge PCR and digital PCR are specific types of amplification reactions well known to those of skill in the art (see for example, but not limited to, Chen et al., Methods Mol Biol., 2011, 231-43; Varley and Mitra, Genome Res., (2008), 1844-50). Amplifying refers to any process of submitting a target nucleic acid to conditions sufficient to allow for amplification of the target nucleic acid if all of the components of the amplification reaction are present. In one embodiment, the nucleic acid amplification reactions disclosed herein can be performed in aqueous solutions, microdroplets, emulsions (such as oil-in water or water-in-oil emulsions), or solid-phase based amplification. Components of an amplification reaction typically include, e.g., primers, target nucleic acids, polymerases, nucleotides, and the like. The term "amplifying" typically refers to an "exponential" increase in target nucleic acids during the amplification reaction. However, "amplifying" as used herein can also refer to linear or non-exponential increases in the numbers of target nucleic acids. Amplification of a target nucleic acid to generate a population of first amplification or first extension products is collectively referred to as a "first amplicon". Further amplification of a first amplicon (e.g., a second round of amplification) to produce a population of second amplification or second extension products is collectively referred to herein as a "second amplicon".

"Polymerase chain reaction" or "PCR" refers to a method whereby a specific fragment or subsequence of a target nucleic acid is amplified, typically in a template dependent manner. Exemplary PCR reaction conditions typically comprise either two or three step cycles. Two step cycles have a denaturation step followed by a hybridization/elongation step. Three step cycles comprise (1) a denaturation step followed by a (2) hybridization step followed by a separate (3) elongation step. Standard PCR conditions for a two or three cycle reaction include a denaturation step at 98° C. for about 1 minute to about 5 minutes on the initial cycle, and about 5 seconds to about 20 seconds for each remaining cycle. A hybridization or annealing step at about 45° C. to about 72° C. or at a Tm (melting temperature) at least 1° C., 2° C., 3° C., or more, below the melting temperature of the pool of primers, for about 10 seconds to about 1 minute. A elongation or extension step at about 68° C. to about 72° C. for about 15 seconds to about 1 minute, typically about 1 min per kilobase of expected product. The extension step is typically between about 5 minutes and about 10 minutes on the last cycle of the PCR reaction, and the reaction mixture is typically held at 4° C. after completion of the final extension. Generally, a PCR reaction will include between 20 to 30 cycles of either the two step or three step PCR conditions described above.

The term "template-dependent manner" typically refers to polynucleotide synthesis of RNA or DNA wherein the sequence of the newly synthesized strand of polynucleotide is complementary to the template, i.e., dictated by the well-known rules of complementary base pairing (see, for example, Watson, J. D. et al., In: Molecular Biology of the Gene, 4th Ed., W. A. Benjamin, Inc., Menlo Park, Calif. (1987)). PCR is well known to those of skill in the art; see, e.g., U.S. Pat. Nos. 4,683,195 and 4,683,202; and PCR Protocols: A Guide to Methods and Applications, Innis et al., eds, 1990.

The term "amplification reaction mixture" or "amplification reagents" as used herein refers to a reaction mixture comprising various reagents necessary to amplify a target nucleic acid. These generally include enzymes, aqueous buffers, salts, primers, target nucleic acids, and nucleoside triphosphates. In some embodiments, an amplification reaction mixture comprises an aqueous solution, microdroplet, emulsion, and/or solid-phase based amplification reaction mixture. In one aspect, an amplification reaction mixture of the instant application can include a microfluidic system or process. Microfluidic processes often employ the use of an emulsion, which contains drops of a dispersed liquid phase surrounded by an immiscible continuous liquid phase (e.g., microdroplets). In some embodiments, a microdroplet comprises an emulsion composition, i.e., a mixture of immiscible fluids (e.g., water and oil). In some embodiments, a microdroplet is an aqueous droplet that is surrounded by an immiscible carrier fluid (e.g., oil). In some embodiments, a microdroplet is an oil droplet that is surrounded by an immiscible carrier fluid (e.g., an aqueous solution). In some embodiments, the microdroplets described herein are relatively stable and have minimal coalescence between two or more microdroplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of microdroplets generated from a sample coalesce with other microdroplets. Microdroplets may be used as reaction vessels for chemical or biological reactions, as storage vessels, and/or as a method to isolate and compartmentalize molecules, such as chemical or biological elements. With proper chemistry such as surfactants on the surface of the emulsion, microdroplets may be made "stable," meaning they are substantially prevented form mixing and merging when in contact with each other. This stability allows one to create a population or library of microdroplets composed of different chemical or biological components that may be stored in the approximately same volume of space without mixing or contamination between and/or among the components of one microdroplet and another. Examples of microfluidic systems and processes capable of forming microdroplets are set forth in U.S. Provisional Patent Applications 61/816,431, 61/870,336, 61/875,312, 61/896,766, 61/905,914, 61/881,040, 61/905,927, 61/934,889, U.S. patent application Ser. Nos. 14/470,860 and 14/786,365, and PCT Publication No. 2014/043388, each of which is incorporated by reference in their entirety. Examples of nucleic acid amplification reactions that can be performed within microdroplets is set forth in U.S. Pat. No. 9,581,549. It will be apparent to one of ordinary skill in the art that other microfluidic systems and processes can be used to design suitable nucleic acid amplification reactions as disclosed herein, wherein the nucleic acid amplification reaction is limited to, or includes, a microdroplet process.

In one aspect, the amplification reaction mixture can comprise a microfluidic process for amplifying the one or more target nucleic acids. In one embodiment, the microfluidic process comprises the formation of a library or population of microdroplets that include one or more target nucleic acids, one or more target-specific primer pairs, a universal primer pair, and other reagents necessary to perform PCR, such as but not limited to, dNTPs, magnesium and a polymerase. In one embodiment, microdroplets allow for the partitioning of target nucleic acids (e.g., genomic DNA) such that an individual microdroplet can comprise a single genomic target. In one embodiment, a microdroplet of the instant application includes a single genomic target in combination with one or more target-specific primer pairs (TSPPs), a universal primer pair, and other reagents so that PCR can be performed on the single genomic target in the microdroplet. In some embodiments, the target nucleic acid or sample is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the microdroplets generated are substantially uniform in shape and/or size. For example, in some embodiments, the microdroplets are substantially uniform in average diameter. In some embodiments, the microdroplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the microdroplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the microdroplets generated are non-uniform in shape and/or size.

In some embodiments, the microdroplets generated are substantially uniform in volume. For example, in some embodiments, the microdroplets generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, the target nucleic acid (e.g., template molecule) is partitioned into a sufficient number of partitions such that TSPP extension can be distinguished from random co-localization. In some embodiments, the partitioning comprises generating at least 1 partition that has 0 copies of the template molecule. In some embodiments, the partitioning comprises generating at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more that have 0 copies of the template molecule. In some embodiments, the partitioning comprises generating at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more that have 0 copies of the template molecule and at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more that have 1 or more copies (e.g., 1, 2, 3, 4, 5, 6, 7, 8, 9, 10 or more copies) of the template molecule.

Partitioning of target nucleic acids (e.g., genomic DNA) into a population or library of microdroplets can also reduce or eliminate cross-over of reagents, amplicons, or TSPPs among the population of microdroplets. Additionally, partitioning improves the ability to efficiently barcode target nucleic acids or amplicons and thereby reduces the likelihood of bias or duplicates when interpreting downstream data, such as NGS data.

Amplification reaction mixtures may also further include stabilizers and other additives to optimize efficiency and specificity. Depending upon the context, the amplification reaction mixture can be provided as a complete or an incomplete amplification reaction mixture. For example, the amplification reaction mixture can be provided as a set of reaction vessels (e.g., Eppendorf™ LoBind microcentrifuge tubes) including all the reagents necessary to conduct the nucleic acid amplification reaction (i.e., a complete amplification reaction mixture). In another embodiment, the amplification reaction mixture can be provided as an incomplete reaction mixture, for example lacking one or more reagents necessary to conduct the nucleic acid amplification reaction (e.g., a series of vessels containing the amplification reagents yet lacking a polymerase). In this embodiment, the reagent necessary for amplification (i.e., a polymerase) may be provided by the user, or optionally provided by another source. Unless otherwise specified or clear from the context, the amplification reaction mixture as used herein, is a complete amplification reaction mixture. In some embodiments, stabilizers such as polyethylene glycol (PEG), Tween 20, Triton X-100, or ethoxylated alky phenol (NP-40)(see for example, but not limited to, U.S. Pat. No. 6,127,155) or polyols (such as glucose, mannitol, galactiol or glucitol) can be present in the amplification reaction mixture. In another aspect, additives such as, but not limited to, 2-pyrrolidine, actemide, and formamide can be present in the amplification reaction mixture. In another embodiment, zwitterionic detergents can be present in the reaction mixture (see for example, but not limited to, U.S. Pat. No. 797,282; US Patent Application No. 20100099150; European Patent 2069487B1, each incorporated herein by reference).

As used herein, the term "partitioning" or "partitioned" refers to separating a sample (e.g., genomic DNA) into a plurality of portions or "partitions." Partitions can be solid or fluid. In some embodiments, a partition is a solid partition, e.g., a microchannel. In some embodiments, a partition is a fluid partition, e.g., a microdroplet. In some embodiments, a fluid partition (e.g., a microdroplet) is a mixture of immiscible fluids (e.g., water and oil). In some embodiments, a fluid partition (e.g., a microdroplet) is an aqueous droplet that is surrounded by an immiscible carrier fluid (e.g., oil). Methods and compositions for partitioning a sample are described, for example, in published patent applications WO 2010/036352, US 2010/0173394, US 2011/0092373, and US 2011/0092376, each of which is incorporated by reference herein in their entireties.

A "primer" refers to a polynucleotide sequence that hybridizes to a complementary sequence on a target nucleic acid and serves as a point of initiation of nucleic acid synthesis. Primers can be of a variety of lengths and are often less than 80 nucleotides in length, for example 20-70 nucleotides, in length. In one embodiment, a full length target-specific primer of the instant application can comprise between 30 and 65 nucleotides in length, such as 30, 35, 40, 45, 50, 55, 60 or 65 nucleotides in length. In some embodiments, a multiplex amplification reaction mixture can include one or more full length target-specific primers having a length of between 30 and 65 nucleotides. Different length target-specific primers may be used in a multiplex amplification reaction such that one or more of the multiplex full length target-specific primers comprises a different nucleotide length as compared to the remainder of the multiplex full length target-specific primer pairs (e.g., a multiplex amplification reaction comprising a first full length target-specific primer having a nucleotide length of 45 nucleotides and a second full length target-specific primer having a nucleotide length of 58 nucleotides). The length and sequences of primers for use in PCR can be designed based on principles known to those of skill in the art, see, e.g., Innis et al., supra. Generally, a primer pair or collection of primers to be used in a nucleic acid amplification of the instant application are designed such that the Tm temperature (melting temperature) of the primer pairs or primer pool are similar (e.g., within 1° C., 1.5° C., 2° C., 2.5° C., 3° C., 3.5° C., 4° C., 4.5° C., 5° C., 5.5° C., 6° C., 6.5° C. or 7° C. of each other). A primer with a Tm temperature significantly higher than the PCR reaction annealing temperate may mis-hybridize and extend at an incorrect location on the target nucleic acid (mis-priming), while a primer with a Tm temperature significantly lower than the PCR reaction annealing temperature may fail to anneal and extend at all (failed priming). Various tools exist for primer design and evaluation (e.g., NCBI-Blast software). In the instant application, primers having highly degenerate sequences may be avoided to reduce the probability of mis-hybridization during the PCR annealing reaction. However, where the target nucleic acids represent genes from different organisms it may be advantageous to use degenerate primers to identify the multitude of organisms present in the reaction mixture. Primers can be DNA, RNA, or a chimera of DNA and RNA portions. In some cases, a primer can include one or more modified nucleosides (e.g., 2-amino-deoxyadenosine or 5-propynyl deoxyuridine) or non-natural nucleotide bases (e.g., uracil in a DNA primer). In some cases, a primer can include a label such as a fluorescent moiety or a FRET donor and FRET acceptor moiety.

As used herein, a "primer pair" refers to two polynucleotide sequences that may be the same or different that hybridize to a locus on a target nucleic acid (e.g., a gene of interest or region of chromosome of interest). Frequently, a primer pair will comprise a forward (upstream) primer and a reverse (downstream) primer that span a region of interest on the target nucleic acid (e.g., one or more exons or one or more introns of a gene). In one embodiment, a forward primer comprises the same polynucleotide sequence as the reverse primer. In another embodiment, a primer pair comprises two polynucleotides sequences that are different (e.g., in nucleotide sequence from a 5' to 3' direction) and that are complementary to a nucleotide sequence within a target nucleic acid, such that extension of the forward primer and/or reverse primer results in amplification of the locus in the target nucleic acid. In one embodiment, the instant application utilizes two or more (e.g., 3, 4, 5, 6, 7, 8, 9, 10, 15, 20, 25, or more) primer pairs in the nucleic acid amplification, wherein each primer pair is specific to a genetic locus, thereby enabling amplification or two or more loci in the same nucleic acid amplification reaction. In one embodiment, the instant application allows for up to 50 primer pairs enabling amplification of 50 different loci in the same single amplification reaction. In some embodiments, the target-specific primer pairs of the instant disclosure have a GC content in the range of between 40-60% such as 45%, 50%, 55% or 60%. In some embodiments, the target-specific primer pairs of the instant disclosure are present in the amplification reaction at the same primer concentration for each target-specific primer pair (e.g., 50 nM). In one embodiment, the target-specific primer pairs of the instant disclosure are present in the amplification reaction at a concentration of between 20 and 100 nM, such as 20 nM, 30 nM, 40 nM, 50 nM, 60 nM, 70 nM, 80 nM, 90 nM or 100 nM. In some embodiments, the target-specific primer pairs of the instant disclosure are present in the amplification reaction at a molar concentration that is lower than the molar concentration of the universal primer pair. In a preferred embodiment, the universal primer pair is present in the amplification reaction at a concentration of between 400 nM and 1000 nM, such as 400 nM, 500 nM, 600 nM, 700 nM, 800 nM, 900 nM or 1000 nM. In some embodiments, the molar concentration of the target-specific primer pairs in the nucleic acid amplification reaction are 2-fold, 3-fold, 4-fold, 5-fold, 10-fold, 20-fold, 30-fold, 40-fold, 50-fold, or more, dilute, as compared to the molar concentration of the universal primer pair (e.g., 20 nM target-specific primer pair versus 1 µM universal primer pair) present in the amplification reaction. In another embodiment, the molar concentration of target specific primer pairs and universal primer pair in an amplification reaction mixture disclosed herein can comprise 2-fold to 10-fold higher than the range of molar concentrations set forth in this paragraph. For example, in some embodiments the molar concentration of a target specific primer pair can comprise between 40 nM and 1000 nM and the molar concentration of the universal primer pair can comprise between 800 nM and 10 µM.

As used herein, "Tm" alone, refers to melting temperature and is the temperature at which one half of a nucleic acid duplex (e.g., a DNA target nucleic acid) will dissociate to become single-stranded. Primer pairs in an amplification reaction mixture can anneal to complementary regions of the single-stranded nucleic acid molecules during hybridization (annealing) and can be extended by the action of a polymerase, for example in a template dependent manner, during an extension step of the nucleic acid amplification reaction.

Figure 2:
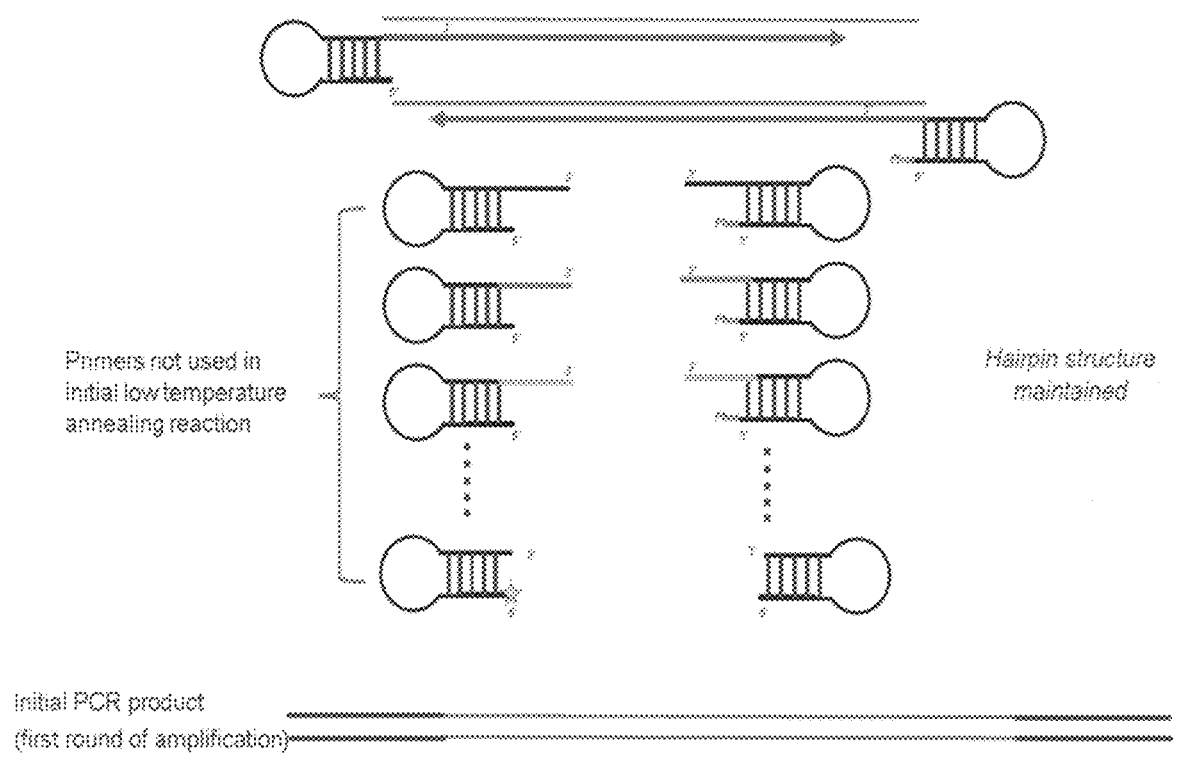
FIG. 2 is a schematic outlining an exemplary PCR reaction of the instant disclosure.
Figure 3:
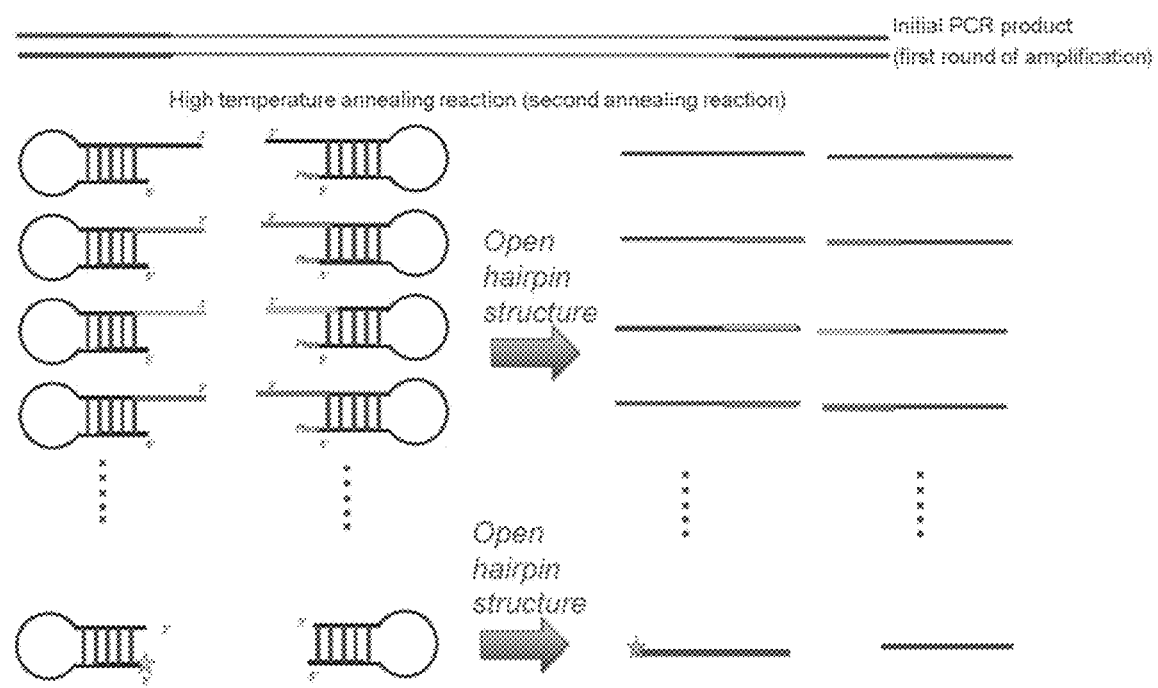
FIG. 3 is a schematic outlining the second amplification reaction of an exemplary PCR reaction of the instant disclosure.
Figure 4:
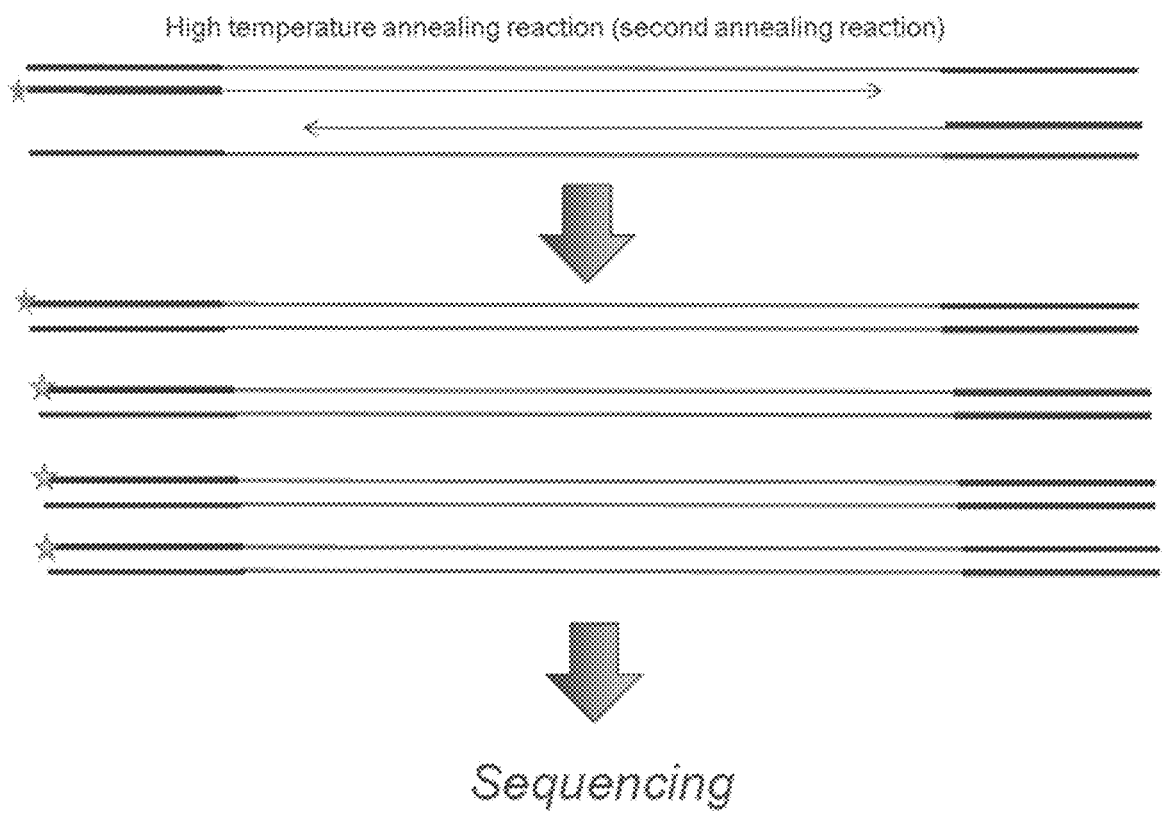
FIG. 4 is a schematic outlining a subsequent step in the second amplification reaction of an exemplary PCR reaction of the instant disclosure.

As used herein, "Tm temperature" refers to primer melting temperature and is the temperature at which 50% of the target-specific primer pairs and/or universal primers present in the nucleic acid amplification reaction mixture are present in linear conformation as opposed to a hairpin conformation. The primers of the instant application (i.e., target-specific primer pairs and universal primer pair) comprise a hairpin (stem-loop), and the hairpin operates as a mechanism to enhance specificity of the nucleic acid amplification reaction based on the annealing temperatures of the PCR amplification reaction. In the nucleic acid amplification reaction set forth herein, a first round of amplification enables target-specific primer pairs to anneal to complementary sequences in target nucleic acids present in the reaction mixture, followed by extension of the target-specific primers by a polymerase to form a population of first amplicons. The annealing temperature in the first round of amplification is set at a Tm temperature that is lower than the melting temperature of the hairpin structures of the primer pairs and the universal primer pair, such that the primer pairs and universal primer pair retain their hairpin conformation. Accordingly these hairpin conformations are not available to bind to complementary nucleic acid sequences in the target nucleic acids and do not serve as a point of initiation of nucleic acid synthesis (see, FIG. 2). A second round of amplification to form second extension products or second amplicons, utilizes a universal primer pair having a hairpin structure including the same 5' region as the target-specific primer pair (i.e., a hairpin structure) and lacking a single-stranded 3' end as determined below the Tm temperature. As discussed above, the universal primer pair during the first annealing step retains its hairpin structure; while during the second annealing step the universal primer pair is transformed under the second annealing temperature, from a hairpin to linear conformation, allowing the universal primer pair to hybridize to a complementary sequence in the first amplicon (i.e., to a universal adaptor sequence located in the 5' region of the first amplicon). Once the linear universal primer pair is annealed to a complementary sequence in the first amplicon, the universal primer pair can be extended by a polymerase, for example in a template dependent manner, to create a population of second extension products or second amplicons. In one embodiment, the first annealing reaction is performed at a Tm temperature below the melting temperature of the universal primer pair such that the universal primer pair in the first annealing reaction remains in a hairpin conformation. In another embodiment, the second annealing reaction is performed at a Tm temperature above the melting temperature of the universal primer pair such that the universal primer pair in the second annealing reaction is present in a linear conformation. In one embodiment, the first annealing reaction is performed at a Tm temperature at least 1° C., 1.5° C., 2° C., 2.5° C., 3° C., 3.5° C., 4° C., or more, below the melting temperature of the universal primer pair such that the universal primer pair in the first annealing reaction remains in a hairpin conformation. In another embodiment, the second annealing reaction is performed at a Tm temperature at least 1° C., 1.5° C., 2° C., 2.5° C., 3° C., 3.5° C., 4° C., or more, above the melting temperature of the universal primer hairpin such that the universal primer pair in the second annealing reaction is in linear conformation.

A nucleic acid, or a portion thereof, "hybridizes" or "anneals" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides. Alternatively, a primer, or portion thereof, can hybridize to a primer binding site if there are fewer than 1 or 2 complementarity mismatches over at least about 10, 12, 14, 16, or 18 contiguous complementary nucleotides. In some embodiments, the temperature at which hybridization between the target-specific primer pairs and the target nucleic acids occurs is room temperature. In some embodiments, the temperature at which hybridization between the target-specific primer pairs and the target nucleic acids occurs is higher than room temperature and lower than the melting temperature of the target-specific primer pairs. In some embodiments, the temperature at which hybridization between the target-specific primer pairs and the target nucleic acids occurs is at least about 37° C., 40° C., 42° C., 45° C., 48° C., 50° C., 52° C., 55° C., 58° C., 60° C., 62° C., 65° C., 68° C., 70° C. or 72° C. In some embodiments, the temperature at which hybridization between the target-specific primer pairs and the target nucleic acids occurs is 37° C., 40° C., 42° C., 45° C., 48° C., 50° C., 52° C., 55° C., 58° C., 60° C., 62° C., 65° C., 68° C., 70° C. or 72° C. In one embodiment, the temperature at which hybridization between the target-specific primer pairs and the target nucleic acids (i.e., first annealing reaction temperature) is 2° C., 3° C., 4° C., 5° C. or 6° C. lower than the second annealing reaction temperature. In another embodiment, the first annealing reaction is performed at a Tm temperature at least 1° C., 1.5° C., 2° C., 2.5° C., 3° C., 3.5° C., 4° C. below the melting temperature of the target-specific primer pairs. In some embodiments, the temperature at which hybridization between the universal primer pair and first amplicons (i.e., second round of amplification) occurs is at least about 40° C., 42° C., 45° C., 48° C., 50° C., 52° C., 55° C., 58° C., 60° C., 62° C., 65° C., 68° C., 70° C., 72° C., 73° C., 74° C., 75° C., 76° C., or higher, where the hybridization of the universal primer pair is performed at a temperature that is at least 2° C. or 1° C. lower than the Tm of the universal hairpin primer, equal to the Tm of the universal hairpin primer, or at least 1° C. higher than the Tm temperature of the universal hairpin primer. In some embodiments, the temperature at which hybridization between the universal primer pair and first amplicons occurs is 40° C., 42° C., 45° C., 48° C., 50° C., 52° C., 55° C., 58° C., 60° C., 62° C., 65° C., 70° C., 72° C., 73° C., 74° C., 75° C., 76° C., or higher, where the hybridization of the universal primer pair is performed at a temperature that is 2° C. or 1° C. lower than the Tm of the universal hairpin primer, equal to the Tm of the universal hairpin primer, or 1° C. higher than the Tm temperature of the universal hairpin primer pair. In some embodiments, the temperature at which hybridization between the universal primer pair and first amplicons occurs is 1° C., 1.5° C., 2° C., 2.5° C., 3.0° C., 3.5° C., 4.0° C., 4.5° C., 5° C., 5.5° C. or 6° C. higher than the first annealing reaction temperature.

As used herein, a "template" or "target nucleic acid" refers to a polynucleotide sequence that comprises the polynucleotide or nucleic acid to be amplified, flanked by one or a pair of primer hybridization sites. Thus, a "template" or "target nucleic acid" comprises the target polynucleotide sequence flanked by hybridization sites for a "forward" primer and/or a "reverse" primer. The target nucleic acid can include any nucleic acid of interest such as DNA, RNA, LNA, PNA, locked nucleic acids, mixtures thereof, and hybrids thereof. A target nucleic acid comprises any nucleotide sequence including one or more nucleotide or nucleoside modifications (e.g., capped or terminated nucleotides) or substitutions (e.g., 8-oxo-dG). In some embodiments, a target nucleic acid is between 30 and about 500 nucleotides in length, preferably between 50 and 300 nucleotides in length. In one embodiment, the target nucleic acid is obtained from one or more organisms. As used here, organism refers to a living or self-replicating particle that is or was previously in existence. The term organism is not necessarily limited to a particular species of organism but also refers to any level of classification. For example the term "organism" but can be used to refer collectively to all of the species within the genus *E. coli* or all of the bacteria within the kingdom eubacteria. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, e.g., *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces* genera); archaeon, such as crenarchaeota, nanoarchaeota or euryarchaeotia; or eukaryotic such as fungi, (e.g., yeasts), plants, protozoans and other parasites, and animals (including insects (e.g., *Drosophila* spp.), nematodes (e.g., *Caenorhabditis elegans*), and mammals (e.g., rat, mouse, monkey, non-human primate and human)).

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases such as, but are not limited to, nitroindole. Modifications can also include 3' and 5' modifications including, but not limited to, capping with a fluorophore (e.g., quantum dot) or another moiety.

As used herein, the term "5' end" or "3' end" when used in reference to a target nucleic acid, primer, target-specific primer pair, hairpin primer, or universal hairpin primer pair refers to the distal ends of a linear nucleic acid molecule. For example, a target-specific primer of the instant application comprises a 5' end and a 3' end, wherein the 3' end comprises a single-stranded region that is target-specific to a nucleic acid of interest to be amplified. In one embodiment, the 3' end of a target-specific primer pair comprises at least 4, 5, 6, 7, 8, 9, 10, 11, 12, 13, 14, 15, 16, 17, 18, 19, 20, 21, 22, 23, 24, 25, 26, 27, 28, 29 or more, nucleotides in length capable of hybridizing to a target nucleic acid of interest. In one embodiment, the 3' end of a target-specific primer pair comprises at least 4, 5, 6, 7, 8, 9, 10, 11, 12, 13, 14, 15, 16, 17, 18, 19, 20, 21, 22, 23, 24, 25, 26, 27, 28, 29 or more, nucleotides that are complementary to a nucleotide sequence present in a target nucleic acid of interest. The target-specific primer pair also contains a 5' end, which includes a 5' region that forms a hairpin when the Tm temperature of the amplification reaction (i.e., the first annealing step) is lower than the Tm of the hairpin primer nucleotide sequence. In one embodiment, the 5' region that forms a hairpin is at least 6, 7, 8, 9, 10, 11, 12, 13, 14, 15, 16, 17, 18, 19, 20, 21, 22, 23, 24, 25, 26, 27, 28, 29, or more nucleotides in length. In one embodiment, the 5' region that forms a hairpin and includes an adaptor sequence is at least 10, 15, 20, 25, 30, 35, or 40 nucleotides in length. In another embodiment, the Tm temperature of the 5' region that forms a hairpin is the Tm temperature of the universal hairpin primer nucleotide sequence. In one embodiment, when the Tm temperature of the nucleic acid amplification reaction is higher than the Tm temperature of the hairpin primer nucleotide sequence, the 5' end of the hairpin primer is present in linear conformation.

As used herein, a "stem loop," also referred to as a "hairpin primer" or "hairpin" refers to a secondary structure formed by a single-stranded oligonucleotide when complementary bases in a first part of the single-stranded oligonucleotide (e.g., the 5' end) hybridize with bases in a second part of the same oligonucleotide (i.e., downstream from the 5' end, including but not limited to, the 3' end of the oligonucleotide) to form a stem structure having intramolecular base-pairing between complementary bases. Optionally, intramolecular base-pairing may not occur along the oligonucleotide to form a loop structure adjacent to the stem structure. In one embodiment, intramolecular base-pairing of the 5' region of the target-specific hairpin primer and/or 5' region of the universal primer may occur across the full length of the oligonucleotide sequence (i.e., from the 5' to the 3' end of the nucleotide sequence). In another embodiment, the complementary base-pairing of the 5' region of the target-specific hairpin primer and/or 5' region of the universal primer may be limited to the stem structure. In some embodiments, the stem structure can include 3, 4, 5, 6, 7, 8, or more, nucleotides in length. In one embodiment, the stem structure is between 4 and 8 nucleotides in length. In some embodiments, the loop structure can comprise 2, 3, 4, 5, 6, 7, or 8, or more nucleotides in length. In one embodiment, the loop structure is between 4 and 8 nucleotides in length.

With respect to hairpin primers of the instant disclosure, at least two different species are present in the disclosed nucleic acid amplification reaction. The first species is the "target-specific primer pair" which comprises one or two target-specific hairpin primers having a 3' single-stranded region that is complementary or capable of hybridizing to a sequence within a target nucleic acid of interest, and a 5' region that forms a hairpin between complementary bases in the 5' region when the Tm temperature is below the melting temperature of the universal hairpin primer nucleotide sequence. The second species of hairpin primer in the nucleic acid amplification reaction is the "universal primer pair" that comprises one or two universal hairpin primers lacking a single-stranded 3' end as determined below the Tm temperature and includes a 5' region as described above for target-specific primer pairs (i.e., includes a nucleotide sequence capable of forming intramolecular base-pairing between complementary bases within the 5' region when the Tm temperature is below the melting temperature of the hairpin nucleotide sequence). For example, nucleotide sequence 5'-ATTGCAGGC-3' is selected as a suitable sequence for preparation of a universal primer; this nucleotide sequence would require further modification to create a hairpin for use in the claimed nucleic acid amplification reaction. One exemplary modification includes modifying the nucleotide sequence such that the universal hairpin primer comprises "5'-ATTGCAGGCGCCTGCAAT-3' (SEQ ID NO:1), where the downstream part of the nucleotide sequence (underlined region) is the reverse complement of the upstream part of the nucleotide sequence, thereby allowing for hairpin formation when the Tm temperature is set below the melting temperature of the full-length or entire nucleotide sequence. Another exemplary modification includes modifying the starting nucleotide sequence (i.e., 5'-ATTGCAGGC-3') to include the nucleotide sequence "5'-ATTGCAGGCTTAAGCAAT-3' (SEQ ID NO:4), where the downstream part of the nucleotide sequence (underlined region) is the reverse complement of the first five nucleotides of the 5' end thereby allowing for a hairpin formation that is not complementary along its full length (i.e., a hairpin having a 5 nucleotide stem and 4 nucleotide loop structure).

In some embodiments, a hairpin of the present disclosure includes complementary base pairing along the full length of the universal primer pair and/or target-specific primer pair nucleotide sequence. In another embodiment, a hairpin of the present disclosure includes complementary base pairing along only part of the universal primer pair nucleotide sequence such that a stem and loop structure are formed, where the loop can be of various sizes. In one embodiment, the loop of a hairpin of the present disclosure can comprise 2, 3, 4, 5, 6, 7, 8, or more, nucleotides in length. In yet an embodiment, the stem of a hairpin of the present disclosure can comprise 2, 3, 4, 5, 6, 7, or 8 nucleotides in length. It is to be understood that the length and the composition (e.g., GC content) of the target-specific hairpin primers and/or universal hairpin primers can be optimized according to buffer composition, hybridization temperature(s) of the nucleic acid amplification reaction, nucleotide sequence of the target-specific hairpin primer or universal hairpin primer, or any portion thereof used to form the target-specific hairpin or universal hairpin structure. In one embodiment, the universal primer pair comprising one or two universal hairpin primers forms a hairpin structure with sufficient thermodynamic stability so as to remain in a closed conformation during the first annealing step and prior to the second annealing step, but that the energy barrier is sufficiently low to allow transformation of the hairpin structure to a linear conformation at the second annealing temperature of the nucleic acid amplification reaction. In another embodiment, the universal primer pair comprising one or two universal hairpin primers is designed such that it is strong enough to remain in a hairpin conformation until the formation of the first amplicon(s) and weak enough so as to remain in linear conformation during the second annealing step and/or formation of the second amplicon(s). In another embodiment, the target-specific primer pair comprising one or two target-specific hairpin primers forms a hairpin structure with sufficient thermodynamic stability so as to remain in a closed conformation during the first annealing step and prior to the second annealing step, such that the 5' region of the target-specific hairpin primers do not serve as points for initiation of nucleic acid synthesis. In contrast, the 3' end of the target-specific hairpin primer comprises a 3' single-stranded region that is complementary or capable of hybridizing to a single-stranded region of a target nucleic acid of interest such that the 3' end acts as a point of initiation for nucleic acid synthesis. A person of ordinary skill in the art will be familiar with factors affecting hybridization and can determine the appropriate lengths for the target-specific hairpin primer and universal hairpin primer for a particular application in order to achieve the above properties.

As used herein, a "target-specific hairpin primer" refers to an oligonucleotide used to amplify a target nucleic acid of interest. In one embodiment, a target-specific hairpin primer comprises a 5' region and 3' region, wherein the 3' region contains a single-stranded nucleic acid sequence that is complementary to a target nucleic acid of interest to be amplified. The 5' region contains a nucleotide sequence that is reverse complementary to a nucleotide sequence located downstream elsewhere in the 5' region such that the 5' region forms a hairpin (e.g., a stem, or stem-loop structure) under suitable reaction conditions. In one embodiment, the 5' region does not contain a nucleotide sequence that is complementary and/or capable of hybridizing to a target nucleic acid of interest to be amplified under the reaction conditions provided. Additionally, the 5' region of the target-specific primer contains a nucleic acid sequence that comprises a universal adaptor sequence to be used in a second amplification step (i.e., second round of amplification to form a second extension product or second amplicon). The target-specific primers of the instant application can comprise multiplex nucleic acid amplification reactions (e.g., 50 target-specific primer pairs or 100 target-specific primers, in a single nucleic acid amplification reaction that allows for the amplification of up to 50 distinct loci). The target-specific primers hybridize under suitable conditions to a target nucleic acid to be amplified and undergo primer extension for example, in a template dependent manner. The extended first primer product (first amplicon) can then be used as a substrate for hybridization by a universal primer pair, to form a population of nucleic acids that are complementary to the first amplicons. As discussed above, the target nucleic acids to be amplified can include, but is not limited to, any nucleic acid such as RNA or DNA and may be obtained or derived from a living or dead organism, or may be obtained from a multiplicity of organisms.

As used herein, the term "first target primer pair" refers to two polynucleotide sequences prepared as a primer pair as defined herein, to amplify a single target nucleic acid of interest. In one embodiment, the "first target primer pair" comprises a reverse (downstream) primer and a forward (upstream) primer to act as initiation sites for DNA or RNA synthesis. Generally, each primer pair of the nucleic acid amplification reaction is designed to hybridize to one loci, so as to prevent mis-hybridization. A first target primer pair comprises at least one forward and/or one reverse primer having a target-specific hairpin primer, wherein the hairpin primer contains a 3' region that is single-stranded and contains a nucleotide sequence that is complementary to or capable of hybridizing to a target nucleic acid to be amplified, and a 5' region that forms a hairpin structure below the Tm temperature of the hairpin nucleotide sequence and forms a linear structure at a Tm temperature above the Tm temperature of the hairpin nucleotide sequence. In one embodiment, the Tm temperature of the 5' region that forms a hairpin can be determined by calculating the melting temperature of the nucleotide sequence that forms the hairpin structure. In another embodiment, the Tm temperature of the 5' region that forms a hairpin can be determined by calculating the melting temperature of the universal hairpin primer. In one embodiment, at least one of the target-specific primers of the first target primer pair comprises a 5' region that forms a hairpin structure below the Tm temperature of the universal hairpin nucleotide sequence and forms a linear structure at a Tm temperature above the Tm temperature of the universal hairpin primer. In one embodiment, both the forward and reverse primer of the first target primer pair include a 5' region that forms a hairpin. In another embodiment, the forward primer of the first target primer pair includes a 5' region that forms a hairpin. In yet another embodiment, the reverse primer of the first target primer pair includes a 5' region that forms a hairpin. In one embodiment, the first target primer pair contains a GC content of between 40-60%. In another embodiment, the Tm temperature of the forward and reverse primers of the first target primer pair are similar to each other (e.g., a Tm temperature within a range of 1-5° C.). In another embodiment, where the first target primer pair is part of a multiplex reaction having a plurality of different target-specific primer pairs (e.g., where different target primer pairs amplify different target nucleic acids of interest), the Tm temperature of the pool of target primer pairs can be similar to each other (e.g., the pool of target primer pairs comprise a Tm temperature that is within a range of 1-5° C.).

As used herein, a "3' single-stranded target-specific region" refers to the 3' end of an oligonucleotide that is in linear, single-stranded form and has a polynucleotide sequence that is complementary to or capable of hybridizing to a target nucleic acid to be amplified. In one embodiment, each target-specific primer pair or target-specific primer in the amplification reaction contains a 3' end having a nucleotide sequence that is complementary along its length or across at least 6, 7, 8, 9, 10, or more continuous nucleotides, to a single loci to enhance the hybridization process. The 3' single-stranded target-specific region can include at least 4, 5, 6, 7, 8, 9, 10, 11, 12, 13, 14, 15, 16, 17, 18, 19, 20, 21, 22, 23, 24, 25, or more, nucleotides in length. In another embodiment, each target-specific primer pair or target-specific primer in the amplification reaction contains a 3' end having a nucleotide sequence that is designed to prevent cross-hybridization with other primers or nucleic acids under the nucleic acid amplification reaction conditions. In one embodiment, the 3' single-stranded target-specific region is between 8 and 30 nucleotides in length, preferably between 12 and 25 nucleotides in length, and more preferably between 20 and 25 nucleotides in length. In one embodiment, the 3' single-stranded target-specific region lacks significant secondary structure such as the potential to form hairpins or primer dimers under the nucleic acid amplification reaction conditions. In some embodiments, the 3' single-stranded target-specific region does not contain highly degenerate nucleic acid sequences. In another embodiment, the 3' single-stranded target-specific region can be complementary to or capable of hybridizing to any target nucleic acid, as defined herein. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin.

As used herein, a "5' region that forms a hairpin" refers to a polynucleotide sequence located at the 5' end of a target-specific hairpin primer pair and/or universal primer pair that forms a hairpin when the target-specific hairpin primer pair or universal primer pair is at a Tm temperature below the melting temperature of the nucleotide sequence that forms the hairpin structure. In one embodiment, the 5' end of a target-specific primer pair or universal primer pair comprises a first nucleotide sequence that is a reverse complement of a nucleic sequence found downstream in the same polynucleotide thereby creating a molecule capable of forming a hairpin configuration under favorable conditions (e.g., at a Tm temperature below the portion of the target-specific hairpin primer pair or universal primer pair that forms the stem structure). In another embodiment, the 5' region fails to form a hairpin if the Tm temperature is higher than the melting temperature of the universal hairpin primer. In another embodiment, the 5' region fails to form a hairpin if the Tm temperature is higher than the melting temperature of the nucleotide sequence of the target-specific primer pair or universal primer pair that forms the stem-loop structure. For example, a Tm temperature during a first annealing step of a nucleic acid amplification reaction that corresponds to the melting temperature of the nucleotide sequence forming the hairpin would result in linear polynucleotides during the annealing step, which can result in non-specific hybridization and spurious amplification products. In one embodiment, the 5' region of the target-specific hairpin primer pair further comprises a universal adaptor sequence of about 4 to about 15 contiguous nucleotides that is a reverse complement to a nucleotide sequence present in the 5' end of the universal hairpin primer pair. In one embodiment, the 5' region of the first target primer pair that forms a hairpin, optionally contains a barcode sequence to allow for indexing of multiple nucleic acid samples (sources) in a single nucleic acid amplification reaction. In another embodiment, the 5' region of the first target primer pair that forms a hairpin, optionally contains a molecular barcode sequence to allow for tagging of amplified nucleic acids such that duplicate reads or errors can be removed, for example during software analysis of downstream sequencing data. Molecular barcoding and indexing of nucleic acid samples are well known in the art, for example Illumina™ sequencing generally utilizes 6 nucleotides to effectively generate 48 or more different barcodes for labelling of nucleic acid samples. The Ion Proton™ and Ion PGM™ sequencer library workflows also use 6 nucleotides to generate 16 or more different barcodes to label nucleic acid samples. US Pat. App. Nos. 2014/041315 and 2016/014274 demonstrate effective molecular barcoding of amplified nucleic acids, thereby improving data obtained in various downstream applications such as deep sequencing where detection of rare mutations or clonal cells within tumors may be useful. In one embodiment, the universal adaptor sequence of the 5' region that forms a hairpin in the target-specific primer pair is complementary to or capable of hybridizing to a nucleotide sequence present in the 5' end of the universal hairpin primer pair. In a further embodiment, a nucleotide sequence having complementarity to the 5' end of the universal primer pair (for example, using part of or substantially all of the universal adaptor sequence) can be prepared such that the nucleotide sequence hybridizes to the universal hairpin primer pair, for example as an immobilized primer used to capture the universal primer pair in a downstream application such as capture-based nucleic acid sequencing.

As used herein, a "universal hairpin primer" refers to a hairpin primer as defined above and includes a 5' region that forms a hairpin under conditions favorable (i.e., at a Tm temperature below the Tm of the universal hairpin primer and does not form a hairpin above the Tm temperature of the universal hairpin primer). The universal hairpin primer lacks a 3' single-stranded-region that is target-specific for the nucleic acid to be amplified. The 5' region of the universal hairpin primer comprises a 5' end having a first nucleotide sequence that is complementary to a second nucleotide sequence found downstream from the 5' end of the same molecule (e.g., the 3' end). As such, the universal hairpin primer allows for specific hybridization of the universal hairpin primer to a first amplification product or first amplicon having a complementary nucleotide sequence to the hairpin, located within the 5' region of the target-specific primer pair nucleotide sequence. By conducting a nucleic acid amplification reaction at a first (low) annealing temperature (e.g., 56° C.) to form a first amplicon, and conducting a second amplification reaction at a second (high) annealing temperature, where the second annealing temperature is higher than, or above, the Tm temperature of the universal hairpin primer pair (e.g., 68° C.), the universal hairpin primer pair present in the second annealing reaction is transformed from a hairpin conformation to a linear configuration thereby allowing the universal hairpin primer pair (now linear) to act as a substrate for primer extension by a polymerase. In some embodiments, the Tm temperature of the universal primer pair is about 2° C. to about 5° C. lower than the Tm temperature of the full length (i.e., 5' region and 3' region) target-specific primer pair or pool of target-specific primer pairs.

A "polymerase" refers to an enzyme that performs template-directed synthesis of polynucleotides, e.g., DNA and/or RNA. The term encompasses both the full length polypeptides and a domain that has polymerase activity, including mutant or modified polymerases that retain polymerase activity. DNA polymerases are well-known to those skilled in the art, including but not limited to, DNA polymerases isolated or derived from *Thermus aquaticus, Pyrococcus furiosus, Thermococcus litoralis,* and *Thermotoga maritime,* or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.). Polymerases include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, a "sample" is meant to include a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a naturally or non-naturally occurring nucleic acids. A sample may also include any body fluid or excretion (for example, but not limited to, blood, serum, amniotic fluid, sperm, urine, stool, saliva, tears, bile) that contains cells, cell components, or nucleic acids. In some embodiments, a sample can include a biopsy or liquid sample obtained from a patient, including but not limited to, a cancer patient that contains nucleic acids such as cell-free circulating tumor DNA (ctDNA). In some embodiments, the sample can include a sample directly obtain from an animal or organism that is optionally purified to isolate or extract cells or target nucleic acids of interest such as a plasma sample from a pregnant animal, including, but not limited to, a pregnant mammal.

As used herein, the term "label" refers to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, 32P and other isotopes, haptens, and proteins which can be made detectable, e.g., by incorporating a label into the nucleotide sequence during extension and/or amplification. The term includes combinations of single labeling agents, e.g., a combination of fluorophores that provides a unique detectable signature, e.g., at a particular wavelength or combination of wavelengths. Any method known in the art for conjugating a label to a desired agent may be employed, e.g., using methods described in Hermanson, Bioconjugate Techniques 1996, Academic Press, Inc., San Diego. In some embodiments, the label may be incorporated or attached to a nucleoside, nucleotide, or resulting double-stranded molecule (e.g., SYBR Green) and can include a ligand or dye, for example, a fluorescent dye such as FAM, DABCYL, TAMRA, JOE, ROX, Cy3, Cy5 or Alexa. In one embodiment, the label can include fluorescence resonance energy transfer (FRET). In one embodiment, a FRET label can include two chromophores that are in close proximity to one another (e.g., the donor and acceptor molecule are located on the same or different oligonucleotide strands). In one embodiment, the label can be incorporated into the 5' region of the universal hairpin primer. In another embodiment, a donor and acceptor molecule can be located at the 5' end of the universal hairpin primer. In one embodiment, the mode of action of the FRET label can include a quenching of the chromophores when the universal hairpin primer is present in a hairpin conformation (e.g., during the first annealing step of the nucleic acid amplification reaction disclosed herein). In another embodiment, the mode of action of the FRET label can include a separation of the chromophores and fluorescence of the donor molecule when the universal hairpin primer is present in a linear conformation (e.g., during the second annealing step of the nucleic acid amplification reactions disclosed herein). In one embodiment, incorporation of a label into one of more of the second extension products (second amplicons) can be detected via emission spectra. In a preferred embodiment, a label is incorporated into each of the second extension products (i.e., second amplicons). In one embodiment, the label acts as an indicator of real-time PCR amplification. In one embodiment, the label can include an AmpliFluor (fluorescein/DABCYL) or Scorpion based oligonucleotides (see for example, but not limited to Nazarenko et al., Nucleic Acids Res., 25, 2516-2521, (1997), Nazarenko et al., J. Histo. Cyctochem., 47(3), 273-279, (1999) and U.S. Pat. No. 6,117,635, all of which are incorporated herein by reference in their entireties.

As used herein, the term "sequencing" and its variants comprises obtaining sequence information from a target nucleic acid, typically by determining the identity of at least one nucleotide (including its nucleobase component) within the target nucleic acid. In some embodiments, "sequencing" includes identifying each and every nucleotide within the target nucleic acid that is sequenced. In another embodiment, "sequencing" can include methods whereby the identity of one or more nucleotides in the target nucleic acid is determined, while the identity of some nucleotides remains undetermined or incorrectly determined. In some embodiments, sequencing comprises obtaining sequence information from a target nucleic acid using next-generation high throughput methods such as single molecule real-time sequencing (e.g., Pacific Biosciences), pyrosequencing (e.g., Roche 454), sequencing by synthesis (e.g., Illumina (Solexa), sequencing by ligation (e.g., SOLiD sequencing), natural nucleotide pH-based sequencing (e.g., Ion Torrent semiconductor sequencing) or nanopore sequencing (e.g., MinION, Oxford Nanopore). In some embodiments, sequencing as used herein includes obtaining RNA from a sample and converting the RNA into complementary DNA (cDNA) using reverse transcriptase. In some embodiments, sequencing includes obtaining RNA from a sample and converting the RNA into complementary DNA (cDNA) using reverse transcriptase prior to performing the nucleic acid amplification reaction of the instant application on the cDNA. In other embodiment, the RNA may be directly amplified using the nucleic acid amplification reaction of the instant application by utilizing primer pairs that are specific for the corresponding RNA target nucleic acid (e.g., primers containing uracil instead of thymine).

I. Introduction

Described herein are methods, kits, and reaction mixtures for target nucleic acid amplification. The disclosure provides novel methods for target nucleic acid amplification by utilizing hairpin primers possessing a Tm temperature (melting temperature) that is dependent on the nucleotide sequence of the hairpin primer. The Tm temperature can be utilized in two distinct annealing steps to increase the specificity of the nucleic acid amplification reaction. In the first annealing step, a target-specific hairpin primer pair anneals to a target nucleic acid under a first (low) Tm temperature and undergoes primer extension, for example in a template dependent manner. In the second annealing step, a universal hairpin primer containing a nucleotide sequence that is complementary to a portion of the target-specific hairpin primer (i.e., universal adaptor sequence) anneals to the product of the first extension reaction at a second (high) annealing temperature and undergoes extension, for example in a template dependent manner. In some embodiments, the methods comprise mixing a first target nucleic acid with a first target primer pair and a universal primer pair, such that a subsequent annealing and extending step results in the production of a population of first amplicons; denaturing the first amplicons into single-stranded molecules; annealing a universal primer pair to the single-stranded molecules and extending the universal primer pair to form second amplicons, thereby amplifying the first target nucleic acid.

In some embodiments, the methods disclosed in the preceding paragraph include a first target primer pair (FTPP) comprising one or two first target-specific hairpin primers (FTSHPs) having a 3' single-stranded target-specific region, at or below a Tm temperature that is complementary to or capable of hybridizing to a target nucleic acid of interest under the annealing conditions, and a 5' region that forms a hairpin below the Tm temperature (melting temperature) of the hairpin of the FTSHPs and/or universal hairpin primer and does not form a hairpin above the Tm temperature of the FTSHPs and/or universal hairpin primer. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin. In some embodiments, the 5' region of the FTSHPs contains a universal adaptor sequence useful for subsequent downstream applications such as nucleic acid sequencing or bioinformatics analysis.

In some embodiments, the method includes a universal primer pair comprising one or two universal hairpin primers (UHPs) having a 5' region that forms a hairpin below the Tm temperature (melting temperature) of the UHPs and does not form a hairpin above the Tm temperature of the UHPs. In some embodiments, the UHPs lack a single-stranded 3' end as determined below the Tm temperature of the UHPs. In some embodiments, the UHPs lack a 3' single-stranded end that is complementary to, or capable of hybridizing to a target nucleic acid under the annealing conditions provided. In some embodiments, the UHPs are capable of forming a stem-loop structure under the annealing conditions provided such that the stem structure creates a blunt-ended molecule (e.g., a hairpin without a 3' or 5' overhang). In some embodiments, the method includes mixing the first target nucleic acid with the first target primer pair and the universal primer pair and annealing the first target primer pairs to the first nucleic acid at a first annealing temperature that corresponds to a temperature below the Tm temperature of the FTSHP; extending the FTSHP with a polymerase to form a first amplicon comprising one or two universal adaptor sequences; denaturing the first amplicon to form two nucleic acid strands and annealing the one or two UHPs to a universal adaptor sequence of one of the nucleic acid strands of the first amplicon at a temperature above the Tm temperature of the FTSHP; extending the one or two UHPs with a polymerase to form a second amplicon, thereby amplifying the first target nucleic acid. In some embodiments, the first annealing temperature corresponds to a temperature that is 3° C., 4° C., 5° C. or 6° C. lower than the second annealing temperature. In another embodiment, the first annealing temperature at least 1° C., 1.5° C., 2° C., 2.5° C., 3° C., 3.5° C. or 4° C. below the melting temperature of the FTSHPs. In another embodiment, the second annealing temperature corresponds to a temperature that is 2° C. or 1° C. lower than the Tm of the universal hairpin primer, equal to the Tm of the universal hairpin primer, or 1° C. or 2° C. higher than the Tm temperature of the universal hairpin primer.

In some embodiments, the disclosure provides kits for performing a target nucleic acid amplification as disclosed in the preceding paragraph. The kits can comprise additional amplification reagents such a buffers, salts, dNTPS and polymerases necessary to perform the amplification methods.

In some embodiments, the disclosure provides reaction mixtures for performing a target nucleic acid amplification reaction. In some embodiments, the reaction mixture comprises one or more target nucleic acids, such as up to 50 different nucleic acids in a single amplification reaction (i.e., a 50-plex reaction). In some embodiments, the nucleic acid amplification reaction comprises up to 50 target-specific primer pairs, where each target-specific primer pair amplifies a distinct target nucleic acid in the amplification reaction, thereby performing a multiplex nucleic acid amplification reaction capable of amplifying up to 50 different target nucleic acids.

II. Methods

Methods of target nucleic acid amplification are provided. The methods include amplification of a single target nucleic acid or the amplification of two or more target nucleic acids. For example, the amplification of up to 50 different target nucleic acids in a single amplification reaction mixture.

Methods of Amplifying a Single Target Nucleic Acid

In some embodiments, methods for amplifying a single target nucleic acid include mixing a first target nucleic acid with (a) a first target primer pair, where the first target primer pair comprises one or two first target-specific hairpin primers, the target-specific hairpin primers having (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence, and (b) a universal primer pair comprising one or two universal hairpin primers (i) having said 5' region, and (ii) lacking a single-stranded 3' end as determined below the Tm temperature; (2) annealing the 3' single-stranded target-specific region of at least one first target-specific hairpin primer from the first target primer pair to the first target nucleic acid at a temperature at or below the Tm temperature and extending the target-specific hairpin primer with a polymerase in a template dependent manner to form a first amplicon comprising one or two universal adaptor sequences; (3) denaturing the first amplicon into two nucleic acid strands; (4) annealing the one or two universal hairpin primers to a universal adaptor sequence of one of the strands of the first amplicon at a temperature above the Tm temperature; and (5) extending the one or two universal hairpin primers with a polymerase in a template dependent manner to form a second amplicon, thereby amplifying the first target nucleic acid. In some embodiments, steps (2) and (3) are repeated multiple times. In some embodiments, steps (2) and (3) are repeated about 5 to about 15 times. In some embodiments, steps (4) and (5) are repeated multiple times. In some embodiments, steps (4) and (5) are repeated about 10 to about 20 times. In some embodiments, step 1 is performed once and steps (2) and (3) are repeated for about 5 to about 15 times before steps (4) and (5) are repeated about 10 to about 20 times. In some embodiments, the first target primer pair is exhausted prior to performing steps (4) or (5). In some embodiments, the first target primer pair is exhausted prior to performing step (4). In some embodiments, the 3' single-stranded target-specific region is single-stranded at a temperature below the Tm temperature of the universal hairpin primer. In some embodiments, the 3' single-stranded target-specific region is single-stranded at a temperature that is above, below, or equal to, the Tm temperature of the universal hairpin primer. In some embodiments, the first annealing temperature is at least 2° C. below the Tm temperature of the universal primer pair and the second annealing temperature is equal to or at least 1° C. above the Tm temperature of the universal primer pair. In some embodiments, the first target primer pair is present in the method at a molar concentration that is about 4-fold to about 50-fold more dilute than the molar concentration of the universal primer pair.

First Target Nucleic Acid

The methods disclosed herein include amplification of a first target nucleic acid. In one embodiment, the first target nucleic acid can comprise any appropriate polynucleotide of interest, such as a DNA, RNA or chimeric nucleic acid sequence of interest (see "target nucleic acid" definition provided herein). In some embodiments, the first target nucleic acid of the method is obtained from, or derived from, a bacterial, viral, or pathogenic organism. In some embodiments, the first target nucleic acid is obtained from, or derived, from a plant, fungal, or animal source. In some embodiments, the first target nucleic acid can be obtained from a human sample, such as a plasma, blood, or tissue sample. In some embodiments, the first target nucleic acid is genomic DNA. In some embodiments, the first target nucleic acid can include one or more introns or exons of one or more genes. In some embodiments, the first target nucleic acid is cDNA, for example obtained by RT-PCR of a RNA sample. In some embodiments, the first target nucleic acid is RNA. In some embodiments, the first target nucleic acid is plasmid DNA. In some embodiments, the first target nucleic acid can include a synthetically prepared (e.g., artificial) nucleic acid sequence of interest. In some embodiments, the first target nucleic acid can include any appropriate polynucleotide sequence that is about 5 nucleotides to about 1000 nucleotides in length, about 10 nucleotides to about 500 nucleotides in length, about 20 nucleotides to about 400 nucleotides in length, about 25 nucleotides to about 250 nucleotides in length, about 30 nucleotides in length to about 150 nucleotides in length, or about 40 nucleotides in length to about 125 nucleotides in length. In some embodiments, the first target nucleic acid can include a polynucleotide sequence that is at least 5, 6, 7, 8, 9, 10, 11, 12, 13, 14, 15, 16, 17, 17, 19, 20, 21, 22, 23, 24, 25, 26, 27, 28, 29, 30, 31, 32, 33, 34, 35, 36, 37, 38, 39, 40 nucleotides, or more, in length. In some embodiments, the first target nucleic acid can comprise one or more polynucleotide modifications along the length of the first target nucleic acid (e.g., a modified nucleoside or nucleotide such as 8-oxo-2'-deoxyguanosine or 5-methylcytosine).

In some embodiments, the first target nucleic acid can be present at a low concentration such that after two, three, four, five, or more, rounds of nucleic acid amplification (e.g., after formation of second amplicons) sufficient amplified first target nucleic acids exist that allow for suitable downstream applications, such as DNA or RNA sequencing, cloning, or genotyping. In one embodiment, the first target nucleic acid may be present in the method at a nanogram, picogram or femtogram amount. In some embodiments, the first target nucleic acid can comprise about 100 ng of DNA, about 75 ng DNA, about 50 ng DNA, about 25 ng DNA, about 10 ng DNA, about 1 ng DNA, about 750 pg DNA, about 500 pg DNA, about 250 pg DNA, about 100 pg DNA, about 10 pg DNA, about 1 pg DNA, about 750 fg DNA, about 500 fg DNA, or less. In some embodiments, the first target nucleic can be present in an amount of about 100 ng of genomic DNA, about 50 ng of genomic DNA, or about 25 ng of genomic DNA. In some embodiments, where the first target nucleic acid is plasmid DNA, the concentration of the first target nucleic acid can comprise about 10 ng of plasmid DNA, about 5 ng of plasmid DNA, about 1 ng of plasmid DNA, about 750 pg of plasmid DNA, about 500 pg of plasmid DNA, about 250 pg of plasmid DNA, about 100 pg of plasmid DNA, or less. It will be readily apparent to one of ordinary skill in the art that the polynucleotide source, or mass, is not a critical parameter providing the method can amplify the first target nucleic acid of interest under the conditions disclosed herein.

First Target Primer Pair

In some embodiments, methods for amplifying a single target nucleic acid include a first target primer pair (FTPP), wherein the FTPP comprises one or two first target-specific hairpin primers (FTSHPs). In one embodiment, the FTPP comprises two target-specific hairpin primers. In some embodiments, only one of the FTPP is a target-specific hairpin primer and the second primer of the FTPP can include a first target-specific linear primer (FTSLP). In one embodiment, a first target-specific linear primer comprises a single-stranded primer that lacks secondary structure and is capable of annealing to the target nucleic acid of interest under the conditions disclosed. In another embodiment, a first target-specific linear primer can comprise a single-stranded primer that lacks sufficient intramolecular base-pairing to form a hairpin structure and comprises a nucleotide sequence that is complementary to or capable of hybridizing to a target nucleic acid of interest. In one embodiment, the FTSHPs include a 3' single-stranded target-specific region at or below a Tm temperature and (ii) a 5' region that forms a hairpin below a Tm temperature (e.g., corresponding to the melting temperature of the universal hairpin primer), and that does not form the hairpin above the Tm temperature of the universal hairpin primer. In some embodiments, the 3' single-stranded target-specific region is single-stranded at a temperature below the Tm temperature of the 5' region that forms a hairpin. In one embodiment, the Tm temperature of the FTSHP minus the 3' target specific region is within 5° C. of the melting temperature of universal hairpin primer. In another embodiment, the Tm temperature of the FTSHP minus the 3' target specific region is within 3° C. of the melting temperature of universal hairpin primer. In yet another embodiment, the Tm temperature of the FTSHP minus the 3' target specific region is within 1° C. of the melting temperature of universal hairpin primer. In some embodiments, the Tm temperature of the FTSHP minus the 3' target specific region is 2° C. lower than the melting temperature of universal hairpin primer. In another embodiment, the Tm temperature of the FTSHP minus the 3' target specific region is at least 2° C. lower than the melting temperature of universal hairpin primer. In yet another embodiment, the Tm temperature of the FTSHP minus the 3' target specific region is more than 3° C. lower than the melting temperature of universal hairpin primer. In some embodiments, the 3' single-stranded target-specific region is single-stranded at a temperature that is above, below, or equal to, the Tm temperature of the 5' region that forms a hairpin. In one embodiment, the Tm temperature of a FTSLP and a FTSHP forming the FTPP in the first annealing step are within 1-5° C. of each other, thereby facilitating specificity during the annealing and extension step. In another embodiment, the Tm temperature of a FTSLP and FTSHP are within 2° C. of each other. In some embodiments, the FTSHPs are not linked to or include a label and are present in the amplification reaction at a molar concentration that is about 4-fold to about 50-fold less than the molar concentration of the universal primer pair in the amplification reaction.

3' Single-Stranded Target-Specific Region

In one embodiment, the 3' single-stranded target-specific region at or below a Tm temperature of a FTSHP or FTSLP comprises at least 5, 6, 7, 8, 9, 10, 11, 12, 13, 14, 15, 16, 17, 18, 19, 20, 21, 22, 23, 24, 25 nucleotides or more, in length that is specific or unique to a first target nucleic acid. In some embodiments, the 3' single-stranded target-specific region comprises a nucleotide sequence that is complementary along its length to an exon, exon-intron junction, and/or intron of a gene, thereby allowing for the detection of the gene using the nucleic acid amplification method. In some embodiments, the 3' single-stranded target-specific region can include a single-nucleotide polymorphism (SNP), thereby allowing for the detection of a single nucleotide variation using the nucleic acid amplification method. In some embodiments, the 3' single-stranded target-specific region comprises a nucleotide sequence that is complementary to a non-coding region of DNA. It will be readily apparent to one of ordinary skill in the art that the length of the 3' single-stranded target-specific region is not critical, as long as the 3' single-stranded target-specific region allows for hybridization of the 3' single-stranded target-specific region of the FTPP to the first target nucleic acid, and that the hybridization remains stable so as to allow for extension of the 3' single-stranded target-specific region of the FTSHP or FTSLP to form a first amplicon. In some embodiments, the FTPP can comprise of a FTSHP and a FTSLP each having a 3' single-stranded target-specific region at or below a Tm temperature comprising about 5, about 6, about 7, about 8, about 9, about 10, about 12, about 13, about 14, about 15, about 16, about 17, about 18, about 19, about 20, about 21, about 22, about 23, about 24, or about 25 nucleotides in length. In some embodiments, the FTPP can comprise a FTSHP and a FTSLP each having a 3' single-stranded target-specific region at or below a Tm temperature, wherein the target-specific regions terminates with a GC or GG clamp (e.g., to aid in the hybridization step). In another embodiment, the method comprises two FTSHPs each having a 3' single-stranded target-specific region as disclosed herein, and a 5' region that forms a hairpin at a temperature below the melting temperature of the FTSHPs and/or the universal hairpin primer. In some embodiments, the 3' single-stranded target-specific region is single-stranded at a temperature below the Tm temperature of the 5' region that forms a hairpin and/or the universal hairpin primer. In some embodiments, the 3' single-stranded target-specific region is single-stranded at a temperature that is above, below, or equal to, the Tm temperature of the 5' region of the FTSHP minus the 3' region that forms a hairpin and/or the universal hairpin primer.

Tm Temperature of First Target-Specific Hairpin Primer

In one embodiment, the methods include mixing a first target primer pair having a 5' region that forms a hairpin below a Tm temperature and that does not form a hairpin above the Tm temperature with a first target nucleic acid in the presence of a universal primer pair. In one embodiment, the 5' region of a FTSHP forms a hairpin when the temperature of the nucleic acid amplification reaction is maintained below the melting temperature (i.e., Tm temperature) of the hairpin. In some embodiments, the melting temperature of the FTSHP corresponds to the temperature (e.g., in Celsius) required to transform the hairpin configuration of the FTSHP to a linear configuration. In one embodiment, the Tm temperature comprises the energy required as measured in Celsius or Fahrenheit to linearize the FTSHP nucleotide sequence (e.g., linearize the stem-loop structure of the 5' region of the FTPP). In some embodiments, the nucleotide sequence corresponding to the stem of a FTSHP is at least 3, at least 4, at least 5, at least 6, at least 7, or at least 8 nucleotides in length. In some embodiments, the nucleotide sequence corresponding to the loop of a FTSHP is at least 3, at least 4, at least 5, at least 6, at least 7, at least 8, at least 9, at least 10, or more nucleotides in length. In one embodiment, the 5' region forming the hairpin structure includes the stem and loop nucleotide sequence. In one embodiment, the step and loop nucleotide sequences comprise at least 6, at least 7, at least 8, at least 9, at least 10, at least 11, at least 12, at least 13, at least 14, at least 15, at least 16, at least 17, at least 18, or more nucleotides in length.

In one embodiment, the Tm temperature of the 5' region of the FTSHP that forms a hairpin can be calculated using any appropriate algorithm available to determine the melting temperature of primers sequences, such as NCBI Blast and Primer3Plus software. The formation of a hairpin is dependent on the stability of the resulting stem and loop nucleotide sequences. The stability of a hairpin is determined for example by its length, the number of mismatches or bulges, and the base composition of the intramolecular paired region. Pairings between guanine and cytosine have three hydrogen bonds and are therefore more stable than adenine-thymine/adenine-thymine pairings that have only two hydrogen bonds. Loops that are less than three bases in length are generally not stable. In one embodiment, the Tm temperature of a hairpin is about 2° C. lower than the melting temperature of the full length (i.e., 5' region and 3' region) of the FTSHP sequence. In another embodiment, the Tm temperature of a hairpin is about 3° C., about 3.5° C., about 4° C., about 4.5° C., about 5° C., or lower than the melting temperature of the FTSHP sequence (i.e., the full length of the FTSHP nucleotide sequence). In some embodiments, the Tm temperature of the hairpin is at least 2° C., at least 2.5° C., at least 3° C., at least 3.5° C., at least 4° C., at least 4.5° C., or at least 5° C. lower than the melting temperature of the full-length FTSHP nucleotide sequence. For example, the following 18-mer (5'-ATT GCA GGC GCC TGC AAT) (SEQ ID NO:1) comprises a nucleotide sequence that could form a hairpin under the conditions disclosed herein. The calculated Tm of this sequence is 57.8° C. If the above 18-mer is appended with a nucleotide sequence corresponding to a 3' single-stranded target-specific region (e.g., nucleotide sequence 5' AAT CCG CTA-3') (SEQ ID NO:2); the resulting FTSHP would comprise 5'-ATT GCA GGC GCC TGC AAT <u>AATTGGCCGCTA</u>-3 (SEC. ID NO:3) and have a Tm of 67.3° C. (underlined region corresponding to the 3' single-stranded target-specific nucleotide sequence). Accordingly, in one embodiment, a FTSHP of the instant application can comprise a 5' region that forms a hairpin, where the hairpin comprises at least two bases that form a stem structure and at least three bases that generate a loop stricture. In some embodiments, the stem structure of the hairpin can comprise one or more additional ($3^4$C base pairings as compared to AT base pairings in the stem structure, to improve the stability of the hairpin. In another embodiment, the Tm temperature of a FTSHP is at least 2° C. higher than the melting temperature of the universal hairpin primer. In another embodiment, the Tm temperature of a hairpin at the 5' end of a FTSHP is equal to the melting temperature of the universal hairpin primer.

Universal Adaptor Sequence

In one embodiment, a FTPP comprises one or two FTSHPs having (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence. In one embodiment, the universal adaptor sequence can comprise about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or more nucleotides in length. In one embodiment, the universal adaptor sequence is at least 15, at least 20, at least 21, at least 22, at least 23, at least 24, at least 25, at least 26, at least 27, at least 28, at least 29, at least 30, at least 31, at least 32, at least 33, at least 34, or more nucleotides in length. In one embodiment, the universal adaptor sequence can comprise 10, 11, 12, 13, 14, 15, 16, 17, 18, 19, 20, 21, 22, 23, 24, 25, 26, 27, 28, 29, 30, 31, 32, 33, 34, or more nucleotides in length. In one embodiment, the universal adaptor sequence of the FTSHPs is complementary to a nucleotide sequence present in one, or both, of the universal hairpin primers. In one embodiment, the universal adaptor sequence is present at the 5' end of the 5' region that forms a hairpin within the FTSHP and is complementary to or capable of hybridizing to a nucleotide sequence present in the 5' region of both universal hairpin primers of the universal primer pair. The universal adaptor sequence allows for the production of one or more second amplicons during a second round of amplification that contain a common (universal) nucleotide sequence flanking the variable, target-specific nucleic acids amplified in the first round of amplification (first amplicons). Simultaneous amplification a plurality of different target-specific nucleic acids (i.e., first amplicons) in a second round of amplification would otherwise require a plurality of primers as opposed to a single universal hairpin primer pair disclosed herein. In one embodiment, the universal adaptor sequence comprises one or more nucleotides from the stem structure and/or one or more nucleotides from the loop structure of the FTSHP as discussed in the preceding paragraph. In one embodiment, the universal adaptor sequence comprises the stem nucleotide sequence of the FTSHP. In another embodiment, the universal adaptor sequence comprises the loop nucleotide sequence of the FTSHP. In one embodiment, the universal adaptor sequence comprises the reverse complement nucleotide sequence in a 5' to 3' direction of a nucleotide sequence present in the 5' region of at least one of the first amplicons.

Universal Primer Pair

In one embodiment, the methods disclosed herein comprise a universal primer pair (UPP). In one embodiment, the universal primer pair comprises one universal hairpin primer (UHP) having a 5' region that is complementary in nucleotide sequence to the 5' region of a FTSHP and lacks the 3' single-stranded target-specific region of the FTSHP. In another embodiment, the universal primer pair can comprise two universal hairpin primers (forward and reverse or upstream and downstream) having the same, or different, nucleotide sequences in 5' to 3' direction. In another embodiment, the universal primer pair comprises two universal hairpin primers (UHPs) each having a nucleotide sequence that is complementary in 5' to 3' direction to the 5' region of two different target-specific hairpin primers and lacking the 3' single-stranded target-specific region as found in the 3' region of the two target-specific hairpin primers. In one embodiment, the 5' region of the UHPs and the 5' region of the FTSHPs comprise a complementary nucleotide sequence across its full length in 5' to 3' direction. In some embodiments, the UHPs may include one or two mismatches as long as the UHPs are capable of hybridizing to the amplified products of the first annealing temperature to generate second amplicons. In some embodiments, the 5' region of the UHPs and the 5' region of the FTSHPs comprise a complementary nucleotide sequence present in the stem and loop structure of the 5' region of the FTSHP. In one embodiment, the universal primer pair (UPP) can include a forward (upstream) universal primer and a reverse (downstream) universal primer of different nucleotide lengths (e.g., 25 nucleotide length for the forward universal primer and 30 nucleotide length for the reverse universal primer). In another embodiment, the forward universal primer can include more, fewer, or equal number of nucleotides in the 5' region that form the UHP as compared to the reverse universal primer. For example, the forward universal primer can comprise 4 nucleotides in the stem and 6 nucleotides in the loop structure as compared to a reverse universal primer having 7 nucleotides in the stem and 5 nucleotides in the loop structure. In one embodiment, the forward and reverse universal primers can comprise two UHPs having a Tm that is within 1° C., 2° C., 3° C., 4° C. or 5° C. of each other.

In some embodiments, a universal hairpin primer of the universal primer pair is linked to a label such that the label is incorporated into a second amplicon during the second extension step. In some embodiments, the 5' end of the universal hairpin primer can include one or more labels such as biotin/streptavidin or a fluorophore, such as a donor molecule (fluorescein) and an acceptor molecule (DABCYL). In one embodiment, the one or more labels can include any one or more of the labels provided in PCT/US2013/025274, PCT/US2011/063654, and U.S. application Ser. No. 14/786,365, the disclosures of which are incorporated herein by reference in their entireties for all purposes. In some embodiments, at least one universal hairpin primer of the universal primer pair is linked to a label that comprises a FRET donor and FRET acceptor molecule. In some embodiments, the UHPs during the first annealing step maintain a hairpin conformation so as not to undergo hybridization to the target nucleic acids. In another embodiment, the UHPs during the second annealing step create a linear conformation so as to undergo hybridization to one or more of the first amplicons. In some embodiments, the UHP pair is present in the amplification reaction at a molar concentration that is at least 1-fold to at least 10-fold greater than the molar concentration of the FTSHPs. In some embodiments, the label at the 5' end of the universal hairpin primer pair can be used to purify or separate the second amplicons from the target nucleic acids, first amplicons, or other components of the amplification reaction mixture. In some embodiment, the label at the 5' end of the universal hairpin primer can be used to detect or quantify the presence or amount of second amplicons present in the amplification reaction. In some embodiments, the label can be used to quantify the amount of second amplicons in the reaction under real-time analysis.

First Annealing Step

In one embodiment, the methods disclosed herein provide for annealing a 3' single-stranded target-specific region of at least one FTSHP from a first target primer pair to a first target nucleic acid at or below the Tm temperature of a hairpin present in the 5' region of the FTSHP or universal hairpin primer and extending the FTSHP with a polymerase in a template dependent manner to form a first amplicon comprising one or two universal adaptor sequences. In one embodiment, the annealing includes conducting an annealing step at a temperature that is at least 2° C. lower than the melting temperature of the 5' region of the FTSHP that forms the hairpin. In another embodiment, the annealing step is conducted at a temperature that is about 3° C., about 3.5° C., about 4° C., about 4.5° C., about 5° C., or lower than the melting temperature of the 5' region of the FTSHP that forms the hairpin. In another embodiment, the annealing step is conducted at a temperature that is equal to, 1° C. or 2° C. lower than the melting temperature of the universal hairpin primer. In another embodiment, the annealing step is conducted at a temperature that is 3° C., 4° C., 5° C. or 6° C. lower than a second annealing step temperature used to generate second amplicons. In some embodiments, annealing a 3' single-stranded target-specific region at or below a Tm temperature in at least one FTSHP from a first target primer pair or a universal primer from a universal primer pair to a first target nucleic acid is performed for a period of at least 10, at least 20, at least 30, at least 40 at least 50, or at least 60 seconds. In some embodiments, the first annealing step is performed for a period of about 10, about 20, about 30, about 40, about 50, or about 60 seconds. In one embodiment, the first annealing step is repeated for about 3 to about 20 cycles, about 5 to about 15 cycles, or about 10 cycles. In another embodiment, the first annealing step and subsequent extension step is repeated until the FTSHPs are exhausted. In one embodiment, the first annealing step can comprise room temperature. In another embodiment, the first annealing step can be at least 37° C., 40° C., 42° C., 45° C., 48° C., 50° C., 52° C., 55° C., 58° C., 60° C., 62° C., 65° C., 70° C., or 72° C. In yet another embodiment, the first annealing step can comprise 37° C., 40° C., 42° C., 45° C., 48° C., 50° C., 52° C., 55° C., 58° C., 60° C., 62° C., 65° C., 70° C., or 72° C. It will be readily apparent to one of ordinary skill in the art that the first annealing step can be modified from the parameters set forth above as long as the 3' single-stranded target-specific region of the FTSHP anneals to a first target nucleic acid and that the 5' region of the FTSHP retains its hairpin configuration during the first annealing step. In some embodiments, the 3' single-stranded target-specific region is single-stranded at a temperature below the Tm temperature of the 5' region that forms a hairpin. In some embodiments, the 3' single-stranded target-specific region is single-stranded at a temperature that is above, below, or equal to, the Tm temperature of the 5' region that forms a hairpin.

First Extension Step

In one embodiment, the method includes extending the FTSHP annealed to a first target nucleic acid in a polymerase template dependent manner. In one embodiment, the polymerase can include a RNA or DNA polymerase, such as Taq DNA polymerase or Phusion® DNA polymerase. In some embodiments, the first extension step can be performed at a temperature below the Tm temperature of the FTSHP 5' region that forms a hairpin. In one embodiment, the extension step comprises a temperature that is at least 2° C. below the Tm temperature of the FTSHP 5' region that forms a hairpin or a universal hairpin primer. In another embodiment, the extension step can comprise a temperature that is about 2° C., about 3° C., about 4° C., or about 5° C. below the Tm temperature of the FTSHP 5' region that forms a hairpin or a universal hairpin primer. In some embodiments, the first extension step can be performed at about 60° C. to about 72° C. provided the extension temperature is below the Tm of the FTSHP 5' region that forms the hairpin. In some embodiments, the first extension step can be performed for about 10 to about 30 seconds. In some embodiments, the first extension step is repeated for about 5 to about 15 times. In some embodiments, the first extension step is repeated 5, 8, 10, 12, 15, 18 or times. In another embodiment, the first extension step can be repeated until the FTSHPs are exhausted. It will be readily apparent to one of ordinary skill in the art that the temperature at which the first extension reaction is performed is not a critical parameter provided the FTSHP remains annealed to the first target nucleic acid before and optionally during the extension step. It will also be readily apparent to one of ordinary skill in the art that the polymerase used to perform extension of the FTSHP can be dependent on the source of nucleic acids (e.g., DNA or RNA) and other considerations, such as accuracy and error rates. For example, the length of the FTSHP or the presence of one or more nucleotide or nucleoside modifications along the target nucleic acid or FTSHP may act to block or slow DNA synthesis by a polymerase.

Denaturing

In one embodiment, the methods disclosed herein provide for denaturing the first amplicon comprising one or two universal adaptor sequences into two nucleic acid strands. Generally, any temperature above the melting temperature of the first amplicon is sufficient to separate the first amplicon into two nucleic acid strands. In some embodiments, the denaturing step can include heating the first amplicon to a temperature of about 90° C. to about 98° C. for about 10 to about 45 seconds, about 15 to about 30 seconds, or about 25 seconds. In some embodiments, the time period for denaturation is at least 15 seconds, at least 20 seconds or at least 30 seconds. It will be readily apparent to one of ordinary skill in the art that the denaturing step can be modified from the parameters set forth above so long as the first amplicons are capable of acting as substrates for one or more universal hairpin primers of the universal primer pair in the second annealing step, discussed below. For example, the first amplicon may not need to be physically separated in its entirety if an incomplete separation of the first amplicon allows at least one of the two universal hairpin primers to anneal to the universal adaptor sequence present in the first amplicon, and allows extension of the universal hairpin primer under conditions favorable for the extension reaction.

Second Annealing Step

In one embodiment, the methods disclosed herein provide for a second annealing step when amplifying a target nucleic acid as discussed in the preceding paragraph. In particular, the methods disclosed herein provide for the annealing of one or two universal hairpin primers to a universal adaptor sequence present in one (or both) of the strands of the first amplicon at a temperature above the Tm temperature of the 5' region of the hairpin primer and/or universal hairpin primer. In one embodiment, the second annealing step includes conducting the second annealing reaction at a temperature that is higher than the first annealing step. In another embodiment, the second annealing step includes an annealing temperature that is higher than the first annealing reaction such that the one or more universal hairpin primers of the universal primer pair transition from a hairpin configuration to a linear configuration during the second annealing step. In some embodiments, the second annealing step includes an annealing temperature that is higher than the first annealing reaction such that the one or more universal hairpin primers of the universal primer pair transition from a hairpin configuration to a linear configuration during the second annealing step and preferably during the second extension step. In one embodiment, the second annealing step can include an annealing temperature that is at least 2°

C., 3° C., 4° C., 5° C., 6° C., 8° C. or even 10° C. higher than the first annealing temperature. In some embodiments, the second annealing step is 2° C., 3° C., 4° C., 5° C., or 6° C. higher than the first annealing temperature. In another embodiment, the second annealing step can include conducting the second annealing step at a temperature equal to the melting temperature of the FTSHP and/or universal hairpin primer. In another embodiment, the second annealing step can comprise an annealing temperature that is about 2° C., about 2.5° C., about 3° C., about 3.5° C., or about 4° C. lower than the melting temperature of the full length FTSHP primer sequence but is equal to or 1° C. higher than the melting temperature of the universal hairpin primer. In some embodiments, the second annealing step of the one or more universal hairpin primers to the universal adaptor sequence of the first amplicon is performed for a period of at least 10, at least 20, at least 30, at least 40 at least 50, or at least 60 seconds. In some embodiments, the second annealing step is performed for a period of 10, 20, 30, 40, 50, or 60 seconds. In one embodiment, the second annealing step is repeated for about 5 to about 15 cycles, about 8 to about 12 cycles, or about 10 to about 20 cycles. It will be readily apparent to one of ordinary skill in the art that the second annealing step described in this paragraph can be modified from the parameters set forth above provided that the universal hairpin primers of the universal primer pair transition from a hairpin configuration to a linear configuration to facilitate annealing of the linear universal primer pair to the universal adaptor sequence present in 5' end of the first amplicon.

Second Extension Step

In one embodiment, the methods disclosed herein provide for a second extension step that results in extension of the one or more universal hairpin primers annealed to the universal adaptor sequence of the first amplicon. In some embodiments, the method includes extending the one or more annealed universal hairpin primers with a polymerase in a template dependent manner. In one embodiment, extension of the one or more universal hairpin primers results in the production of a second amplicon, thereby amplifying the first target nucleic acid. In one embodiment, the second extension step comprises a temperature that is at least 1° C. or 2° C. above the Tm temperature of the FTSHP and/or universal hairpin primer. In another embodiment, the second extension step comprises a temperature that is about 2° C., about 3° C., about 4° C., or about 5° C. above the Tm temperature of the 5' region of the FTSHP that forms the hairpin and/or universal hairpin primer. In some embodiments, the second extension step can be performed at about 62° C. to about 72° C. provided the extension temperature is above the Tm temperature of the 5' region that forms the FTSHP. In some embodiments, the second extension step can be performed for about 10 to about 30 seconds. In some embodiments, the second extension step is repeated for about 10 to about 20 times. In another embodiment, the second extension step is repeated until the amount of PCR product is sufficient for any appropriate downstream application such as next-generation sequencing. In one embodiment, the second extension step is repeated uniformly until the final cycle wherein the second extension step can be performed for about 1 minute to about 5 minutes to ensure extension of the amplification product(s) is complete. It will be readily apparent to one of ordinary skill in the art that the temperature at which the first extension reaction is performed is not a critical parameter provided the FTSHP remains annealed to the first target nucleic acid before and optionally during the extension step. It will be readily apparent to one of ordinary skill in the art that the polymerase used to perform the second extension step can be the same or a different polymerase from the first extension reaction. In one embodiment, the polymerase used to perform the first and second extension steps are the same polymerase, so as to generate a single, closed-tube nucleic acid amplification reaction. It will also be apparent to one of skill in the art that the polymerase used in the second extension reaction can be dependent on the source of nucleic acids to be amplified (e.g., DNA or RNA) and other considerations, such as accuracy and error rates. For example, the length of a universal primer, or the presence of one or more nucleotide or nucleoside modifications along the target nucleic acid may act to block or slow DNA synthesis by a polymerase. It will be readily apparent to one of ordinary skill in the art that the second extension step can be modified from the parameters set forth herein as long as one (or both) universal hairpin primer is extended to an extent that the second amplicons reflect the nucleotide sequence of the first amplicon(s). In one embodiment, the second extension reaction can include a RNA or DNA polymerase, such as Taq DNA polymerase, 9° N DNA polymerase, or Phusion® DNA polymerase. Other polymerases including, but not limited to, thermostable DNA polymerases are considered routine and foreseeable substitutions to the methods disclosed herein.

Multiplex Method for Amplifying One or More Target Nucleic Acids

In some embodiments, methods for amplifying two or more target nucleic acids include (1) mixing two or more target nucleic acids with (a) a first and second target primer pair, where the first and second target primer pairs each comprise one or two target-specific hairpin primers for different ones of the two or more target nucleic acids, wherein the first and second target-specific hairpin primers have (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence, and (b) a universal primer pair comprising one or two universal hairpin primers (i) having said 5' region, and (ii) lacking a single-stranded 3' end as determined below the Tm temperature; (2) annealing the 3' single-stranded target-specific region of at least one first target-specific hairpin primer from the first target primer pair to a first target nucleic acid at a temperature at or below the Tm temperature and extending the first target-specific hairpin primer with a polymerase in a template dependent manner to form a first amplicon comprising one or two universal adaptor sequences and annealing the 3' single-stranded target-specific region of at least one second target-specific hairpin primer from the second target primer pair to a second target nucleic acid at a temperature at or below the Tm temperature and extending the second target-specific hairpin primer with a polymerase in a template dependent manner to form a first extension product comprising one or two universal adaptor sequences; (3) denaturing the first amplicon and the first extension product into two nucleic acid strands; (4) annealing the one or two universal hairpin primers to a universal adaptor sequence of one of the strands of the first amplicon at a temperature above the Tm temperature and annealing the one or two universal hairpin primers to a universal adaptor sequence of one of the strands of the first extension product at a temperature above the Tm temperature; and (5) extending the one or two universal hairpin primers with a polymerase in a template dependent manner to form a second amplicon or a second extension product, thereby amplifying the two or more target nucleic acids. In some embodiments, the 3' single-stranded target-specific region is single-stranded at a temperature below the Tm temperature of the 5' region that forms a hairpin and/or universal hairpin primer. In some embodiments, the 3' single-stranded target-specific region is single-stranded at a temperature that is above, below, or equal to, the Tm temperature of the 5' region that forms a hairpin.

In some embodiments, the methods disclosed herein comprise mixing three or more target primer pairs to amplify three or more different target nucleic acids. In one embodiment, the three or more target primer pairs each comprise two target-specific hairpin primers having a 3' single-stranded target-specific region at or below a Tm temperature and a 5' region that forms a hairpin below a Tm temperature and that does not form a hairpin above the Tm temperature, wherein the 5' region comprises a universal adaptor sequence, and the 3' single-stranded target-specific region is designed to amplify a different target nucleic acid. In one embodiment, each target primer pair is designed such that two target-specific hairpin primers amplify a distinct target nucleic acid (e.g., a single loci) as compared to other target primer pairs present in the amplification, thereby minimizing cross-hybridization. In one embodiment, each of the target primer pairs of a multiplex nucleic acid amplification comprise one forward (upstream) target-specific primer and one reverse (downstream) target-specific primer for each target nucleic acid to be amplified. In some embodiments, the method comprises mixing up to 50 different target primer pairs to amplify up to 50 different target nucleic acids. In one embodiment, the method comprises mixing 25-100 target primer pairs comprising 25-100 different forward target primers having a 3' single-stranded region wherein each 3' region is target-specific for an individual loci, and a 5' region that forms a hairpin below a Tm temperature and that does not form the hairpin above the Tm temperature, and 25-100 different reverse target primers having a 3' single-stranded region wherein each 3' region is target-specific for an individual loci, and a 5' region that forms a hairpin below a Tm temperature and that does not form the hairpin above the Tm temperature, thereby allowing for the amplification of 25-100 different target nucleic acids. In another embodiment, the method comprises mixing 40-60 target primer pairs comprising 40-60 forward target primers each having a 3' single-stranded region distinct from the 3' single-stranded region of another forward target primer in the primer pool, and 40-60 reverse target primers each having a 3' single-stranded region distinct from the 3' single-stranded region of another reverse target primer in the primer pool, thereby allowing for the amplification of 40-60 distinct target nucleic acids.

In one embodiment, multiplex nucleic acid amplification reactions disclosed herein can comprise 2, 5, 8, 10, 12, 15, 20, 25, 30, 35, 40, 45, 50, 55, 60, 65, 70, 75, 80, 85, 90, 95, or 100 target-specific primer pairs enabling nucleic acid amplification of up to 100 different target nucleic acids in a single amplification reaction. In some embodiments, the target-specific primer pairs may be designed to amplify specific genes or portions thereof (e.g., exons or SNPs) associated with one or more diseases or conditions. For example, target-specific primer pairs can be designed to amplify genes associated with inherited diseases such as inherited cardiomyopathy and cardiac arrhythmias, pulmonary, renal, hematology, autism, deafness, metabolic function, ophthalmic, neurological, primary immune deficiency, dermatology, endocrine, epilepsy, gastrointestinal, cystic fibrosis and cancers (i.e., ovarian cancer), see for example, Ion Ampliseq™ Inherited Disease Gene Panels, Life Technologies Corp., Carlsbad, Calif. In one embodiment, target-specific primer pairs can be designed to amplify genes associated with infectious diseases such as tuberculosis and Ebola, see for example, Ion Ampliseq™ Infectious Disease Gene Panels, Life Technologies Corp., Carlsbad, Calif. In another embodiment, target-specific primer pairs can be designed to amplify genes associated with human identification which may be particularly useful for forensic analysis or predicting eye and hair color. For example, see DNA phenotyping panel, Human Identification Identity panel and Human Identification Ancestry panel offered by Ion Ampliseq™ Gene Panels, Life Technologies Corp., Carlsbad, Calif. In yet another embodiment, target-specific primer pairs of the instant disclosure can be designed to amplify one or more genes or a fragment thereof (e.g., a cancer hotspot mutation) associated with brain, breast, colon, ovarian, pancreatic, prostate, renal, uterine or other cancers. In one embodiment, target-specific primer pairs of the instant disclosure can be designed to amplify one or more genes or a fragment thereof selected from the group consisting of ABL1, AIP, AKT1, ALK, APC, ATM, BAP1, BARD1, BLM, BRAF, BRCA1, BRCA2, BRIP1, BMPR1A, CDH1, CDK4, CDKN1B, CDKN2A, CHEK2, CSF1R, CTNNB1, DICER1, EGFR, EPCAM, ERBB2, ERBB4, EZH2, FANCC, FBXW7, FGFR1, FGFR3, FH, FLCN, FLT3, GALNT12, GNA11, GNAQ, GNAS, GREM1, HOXB13, HRAS, IDH1, IDH2, JAK2, JAK3, KDR, KIT, KRAS, MAX, MEN1, MET, MITF, MLH1, MPL, MRE11A, MSH2, MSH6, MUTYH, NBN, NF1, NF2, NOTCH1, NPM1, NRAS, PALB2, PDGFRA, PHOX2B, PIK3CA, PMS2, POLD1, POLE, POT1, PRKAR1A, PTCH1, PTEN, PTPN11, RAD50, RAD51C, RAD51D, RB1, RET, SDHA, SDHAF2, SDHB, SDHC, SDHD, SMAD4, SMARCA4, SMARCB1, SMARCE1, SMO, STK11, SUFU, TMEM127, TP53, TSC1, TSC2, VHL, and XRCC2.

In some embodiments, target-specific primer pairs can include one or more housekeeping genes to observe gene expression and/or act as a positive control for nucleic acid amplification. For example, commercially available PCR kits exist for various housekeeping genes and may optionally be combined with labels during the multiplex nucleic acid amplification reaction such as SYBR-Green, see for example RT Profiler™ PCR Array Housekeeping Genes, Qiagen, Inc., (Germantown, Md., USA) including PCR arrays for cow, pig, horse, fruit fly, rat, zebrafish, mouse, Chinese hamster, dog, chicken, and human. In yet another embodiment, target-specific primer pairs of the instant disclosure can be designed to amplify one or more human genes for experimental calibration/PCR control genes e.g., one or more genes selected from Table 1.

TABLE 1

| Gene Name | RefSeq accession number | Gene description | Genomic coordinates (hg19) of strongly and uniformly expressed exons | | |
|---|---|---|---|---|---|
| C1orf43 | NM_015449 | chromosome 1 open reading frame 43 | chr1 | 154192817 | 154192883 |
| | | | chr1 | 154186932 | 154187050 |
| | | | chr1 | 154186368 | 154186422 |
| | | | chr1 | 154184933 | 154185100 |
| | | | chr1 | 154184795 | 154184854 |

TABLE 1-continued

| Gene Name | RefSeq accession number | Gene description | Genomic coordinates (hg19) of strongly and uniformly expressed exons | | |
|---|---|---|---|---|---|
| CHMP2A | NM_014453 | charged multivesicular body protein 2A | chr19 | 59065411 | 59065579 |
| | | | chr19 | 59063625 | 59063805 |
| | | | chr19 | 59063421 | 59063552 |
| EMC7 | NM_020154 | ER membrane protein complex subunit 7 | chr15 | 34382517 | 34382656 |
| | | | chr15 | 34380253 | 34380334 |
| | | | chr15 | 34376537 | 34376687 |
| GPI | NM_000175 | glucose-6-phosphate isomerase | chr19 | 34857687 | 34857756 |
| | | | chr19 | 34859487 | 34859607 |
| | | | chr19 | 34868639 | 34868786 |
| | | | chr19 | 34869838 | 34869910 |
| | | | chr19 | 34872370 | 34872424 |
| | | | chr19 | 34884152 | 34884213 |
| | | | chr19 | 34884818 | 34884971 |
| | | | chr19 | 34887205 | 34887335 |
| | | | chr19 | 34887485 | 34887562 |
| | | | chr19 | 34890111 | 34890240 |
| | | | chr19 | 34890460 | 34890536 |
| | | | chr19 | 34890623 | 34890690 |
| PSMB2 | NM_002794 | proteasome subunit, beta type, 2 | chr1 | 36101910 | 36102033 |
| | | | chr1 | 36096874 | 36096945 |
| | | | chr1 | 36070833 | 36070883 |
| PSMB4 | NM_002796 | proteasome subunit, beta type, 4 | chr1 | 151372456 | 151372663 |
| | | | chr1 | 151372917 | 151373064 |
| | | | chr1 | 151373239 | 151373321 |
| | | | chr1 | 151373714 | 151373831 |
| RAB7A | NM_004637 | member RAS oncogene family | chr3 | 128525214 | 128525433 |
| | | | chr3 | 128526385 | 128526514 |
| | | | chr3 | 128532169 | 128532262 |
| REEP5 | MM_005669 | receptor accessory protein 5 | chr5 | 112256859 | 112256953 |
| | | | chr5 | 112238076 | 112238215 |
| | | | chr5 | 112222711 | 112222880 |
| SNRPD3 | MM_004175 | small nuclear ribonucleoprotein D3 | chr22 | 24953642 | 24953768 |
| | | | chr22 | 24963951 | 24964144 |
| VCP | NM_007126 | valosin containing protein | chr9 | 35067887 | 35068060 |
| | | | chr9 | 35066671 | 35066814 |
| | | | chr9 | 35064150 | 35064282 |
| | | | chr9 | 35062213 | 35062347 |
| | | | chr9 | 35061999 | 35062135 |
| | | | chr9 | 35061573 | 35061686 |
| | | | chr9 | 35061011 | 35061176 |
| | | | chr9 | 35060797 | 35060920 |
| | | | chr9 | 35060309 | 35060522 |
| | | | chr9 | 35059489 | 35059798 |
| | | | chr9 | 35059060 | 35059216 |
| | | | chr9 | 35057372 | 35057527 |
| | | | chr9 | 35057116 | 35057219 |
| VPS29 | NM_016226 | vacuolar protein sorting 29 homolog | chr12 | 110930800 | 110931036 |
| | | | chr12 | 110929812 | 110929927 |

In yet another embodiment, target-specific primer pairs of the instant disclosure can be designed to amplify one or more housekeeping bacterial genes for experimental calibration/PCR control genes e.g., one or more genes selected from Table 2.

TABLE 2

| 23SrRNA | 6PGDH | adk | alaS | aroE | asnA | atpA | atpB | BBPR_0375 |
|---|---|---|---|---|---|---|---|---|
| BBPR_0429 | BBPR_0603 | BC_1223 | bgluc | BT9727_4034 | BT9727_4549 | BT9727_5154 | cca | coaE |
| CSP | CT147 | cysG | cysS | ddlA | degP | dfrA | dnaG | efp |
| era | fabD | Fer | fopA | fotI | ftsZ | fusA | gap | gatB_Yqey |
| glcK | glgX | glnA | glnD | glpR | gltX | gluC | gluD | glyA |
| gmk | gpm | groEL | GSP | gukl | gyrA | gyrB | hcaT | hemF |
| hemN_2 | hycG | icdA | idnT | ihfB | IleS | ilvD | ilvY | IspD |
| ldhD | lpxC | map | metL | mrp | mur | murG | nadD | nadph |
| ndh | nifU | nth | oppA_2 | pbpC | pdxS | petB | pflC | pheS |
| phnN | pldA | plsC | pntA1 | polA | ppc | proC | prsA | pspA |
| pta | purB | purC | pyk | pyrH | queF | radA | recA | recF |
| rfe | rho | ribC | ribF | rimM | rnpA | rnpB | rpL11 | rpL4 |
| rplD | rplI | rpoA | rpoB | rpoC | rpoD | rps1B | RpS7 | rpsJ |
| rpsU | rraA | 16SrRNA | sdhA | secA | sodA | ssrA | tkt | tmRNA |

TABLE 2-continued

| tpi | tpiA | trpS | tuf | tyrP_2 | tyrS | udp | ugpQ | uvrD |
|---|---|---|---|---|---|---|---|---|
| uxuB | uxuR | yadH | yaeI | yafS | yajR | yghB | ygjD | yhbN |
| yraL | | | | | | | | |

In some embodiments, the second amplicons or second extension products obtain by the methods disclosed herein can be using in any appropriate downstream application. In one embodiment, the second amplicons or second extension products can be utilized in nucleic acid sequencing methods, as the input DNA or RNA for a next-generation sequencing reaction. In some embodiments, the second amplicons or second extension products may be optionally isolated, extracted, or purified from one or more target nucleic acids in the amplification reaction prior to sequencing. In some embodiments, the second amplicons and/or second extension products can be used in high-throughput sequencing. In some embodiments, the second amplicons can be isolated or compartmentalized, for example, distributed into emulsions or micelles. In some embodiments, the second amplicons can be dispersed into emulsions such that on average, each emulsion contains a single, second amplicon. In some embodiments, the emulsions can be used for nucleic acid amplification and/or sequencing.

Methods for high-throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511,803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina Inc., and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

For example the Ion Torrent technology is a method of DNA sequencing that may be used in conjunction with the present invention. Ion Torrent sequencing is based on the detection of hydrogen ions that are released during polymerization of DNA (See, e.g., Science 327(5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The benefits of ion semiconductor sequencing are rapid sequencing speed and low upfront and operating costs.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed template DNA is subjected to strand extension using a fluorescently-modified polymerase and florescent acceptor molecules, resulting in detectible fluorescence resonance energy transfer (FRET) upon nucleotide addition. In one aspect, the primer template DNA of the single molecule sequencing method of Voelkerding et al., may be replaced with the second amplicon or second extension products of the instant application and undergo strand extension using the fluorescently modified polymerase and florescent acceptor molecules. It will be readily apparent that other high throughput sequencing methods may be modified to incorporate the second amplicons or second extension products as the template DNA in the sequencing methods known in the art.

III. Kits

In one aspect, kits are provided for amplifying a target nucleic acid. In some embodiments, a kit includes (a) a first target primer pair (FTPP), the FTPP comprising one or two first target-specific hairpin primers (FTSHPs) having (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence, and (b) a universal primer pair comprising one or two universal hairpin primers (i) having said 5' region, and (ii) lacking a single-stranded 3' end as determined below the Tm temperature. In some embodiments, the 3' single-stranded target-specific region is single-stranded at a temperature below the Tm temperature of the 5' region that forms a hairpin and/or universal hairpin primer. In some embodiments, the 3' single-stranded target-specific region is single-stranded at a temperature that is above, below, or equal to, the Tm temperature of the 5' region that forms a hairpin and/or universal hairpin primer. In one embodiment, the kit can include an FTPP that comprises two target-specific hairpin primers. In another embodiment, the kit can include an UPP that comprises two universal hairpin primers. In some embodiments, the universal primer pair is present in the kit in a quantity greater than the quantity of the first target primer pair. In some embodiments, the universal primer pair is present in a 2-fold, 3-fold, 4-fold, 5-fold, 10-fold, 15-fold, 20-fold, 30-fold, 40-fold, 50-fold or even greater amount as compared to the quantity of the first target primer pair. In some embodiments the first target primer pair of the kit is not linked to a label. In some embodiments, at least one universal hairpin primer of the universal primer pair is linked to a label. In some embodiments, the universal hairpin primer is linked to fluorophore. In some embodiments, the label present on the universal hairpin primer can comprise a FRET donor and FRET acceptor moiety.

In some embodiments, the kit can further comprise a second target primer pair comprising one or two second target-specific hairpin primers, the second hairpin primers having (i) a 3' single-stranded target-specific region different from the 3' single-stranded target-specific region of the first target-specific hairpin primers and (ii) said 5' region. In one embodiment, the kit can further include 5, 10, 15, 20, 25, 30, 35, 40, 45, 50, 60, 70, 80, 90, 100 or more, additional target primer pairs, wherein each additional target primer pair comprises one or two target-specific hairpin primers, wherein the additional target-specific hairpin primers include a (i) a 3' single-stranded target-specific region different from the 3' single-stranded target-specific region of any other target-specific hairpin primer present in the kit and (ii) said 5' region. In some embodiments, the 3' single-stranded target-specific region of each target-specific hairpin primer pair are single-stranded at a temperature below the Tm temperature of the 5' region that forms a hairpin and/or universal hairpin primer. In some embodiments, the 3' single-stranded target-specific region is single-stranded at a temperature that is above, below, or equal to, the Tm temperature of the 5' region that forms a hairpin and/or universal hairpin primer.

In some embodiments, the kit can be provided in a single container. In some embodiments, the kit can be provided in multiple containers or vessels. In some embodiments, the kit further comprises amplification reagents necessary to amplify the one or more target nucleic acids using the methods disclosed herein. In some embodiments, the amplification reagents can include one or more polymerases, amplification buffers, salts, and dNTPs. In some embodiments, the kit can include one or more additional stabilizers and/or additives to improve the yield, specificity, or accuracy of the nucleic acid amplification reaction.

IV. Reaction Mixtures

Reaction mixtures are provided for amplifying a target nucleic acid. In some embodiments, the reaction mixture can include (1) a sample having one or more target nucleic acids, and (2) a first target primer pair (FTPP), the FTPP comprising one or two first target-specific hairpin primers (FTSHPs) having (i) a 3' single-stranded target-specific region at or below a Tm temperature and (ii) a 5' region that forms a hairpin below a Tm temperature and that does not form the hairpin above the Tm temperature, wherein the 5' region comprises a universal adaptor sequence, and (b) a universal primer pair (UPP) comprising one or two universal hairpin primers (i) having said 5' region, and (ii) lacking a single-stranded 3' end as determined below the Tm temperature.

In one embodiment, the reaction mixture further comprises amplification reagents for amplifying at least one of the one or more target nucleic acids present in the sample. In one embodiment, the reaction mixture comprises a FTPP that comprises two target-specific hairpin primers. In another embodiment, the reaction mixture comprises a UPP having two universal hairpin primers, wherein the two universal hairpin primers include (1) the said 5' region and lack a single-stranded 3' end as determined below the Tm temperature. In some embodiments, the UPP is present in the reaction mixture in a quantity greater than the quantity of the first target primer pair. In some embodiments, the UPP is present in a 2-fold, 3-fold, 4-fold, 5-fold, 10-fold, 15-fold, 20-fold, 30-fold, 40-fold, 50-fold, or even greater amount, as compared to the quantity of the first target primer pair. In some embodiments, the first target primer pair of the reaction mixture is not linked to or includes a label. In some embodiments, at least one universal hairpin primer of the UPP is linked to or includes a label. In some embodiments, at least one universal hairpin primer of the UPP is linked to fluorophore. In some embodiments, the number of target nucleic acids that can amplified in the reaction mixture is limited to the number of target-specific primer pairs present in the reaction mixture. In some embodiments, the number of target-specific primer pairs in the reaction mixture is between, 1 and 10, 1 and 20, 1 and 30, 1 and 40, or 1 and 50 target-specific primer pairs. In one embodiment, the number of target-specific primer pairs can include up to 50 different target-specific primer pairs. It will be readily apparent to one of skill in the art, that as the number of target-specific primer pairs increases, the Tm temperature of the pool of target-specific primer pairs may shift up or down from a common or similar melting temperature. In one embodiment, the target-specific primer pairs of the reaction mixture have a Tm temperature that is within 1° c. to 5° C. of any other target-specific primer pair in the reaction mixture.

All patents, patent applications, and other publications, including GenBank Accession Numbers, cited in this application are incorporated by reference in the entirety for all purposes.

EXAMPLES

The following examples are provided by way of illustration only and not by way of limitation. A variety of non-critical parameters can be changed or modified to yield essentially the same or similar results.

Example 1: Universal Primer Strategy, and Overview

An overview of an exemplary universal primer strategy and process is provided in FIGS. 1-4. In brief, a nucleic acid amplification reaction mixture comprising multiplex target-specific primer pairs is designed having a 3' single-stranded target-specific region, and a 5' region that forms a hairpin below the melting temperature and that does not form a hairpin above the melting temperature. The 5' region of the target-specific primer pairs contains a first nucleotide sequence and a second nucleotide sequence that are complementary to each other, to form a stem of the hairpin. The 5' region also contains a nucleotide sequence that acts as a universal adaptor sequence for subsequent amplifications (e.g., a nucleotide sequence in the loop of the hairpin and/or in the stem of the hairpin). The nucleic acid amplification reaction mixture also contains a universal primer pair, where the universal primer pair lacks a 3' single-stranded target-specific region, and includes a nucleotide sequence that can include: (1) a nucleotide sequence that is identical to the 5' region of the single-stranded target-specific primer, (2) a nucleotide sequence that is complementary to the nucleotide sequence present in the adaptor sequence, and (3) is complementary to the 3' end of the universal hairpin primer to form a hairpin structure.

The universal primer pair can comprise one or two universal hairpin primers as described above. The hairpin is designed to remain "closed" during a first nucleic acid amplification reaction because the annealing temperature of the first nucleic acid amplification reaction is below the Tm temperature of the universal hairpin primer present in the amplification reaction mixture. Additionally, the universal primer pair is present in the first nucleic acid amplification reaction in a higher concentration as compared to the concentration of the target-specific primer pairs, which are present in low abundance and are typically exhausted prior to the termination of the first round of nucleic acid amplification. By having two components of the first nucleic acid amplification reaction in a closed-loop hairpin configuration (i.e., the target-specific primer pair(s) and universal primer pair), the universal primer pair cannot act as a point of initiation for primer extension because the universal primer pair cannot hybridize to the target nucleic acids in the reaction mixture because the universal primer pair lacks a 3' single-stranded target-specific region that is complementary to or capable of hybridizing to the target nucleic acids. To the contrary, the target-specific primer pairs have a 3' single-stranded nucleic acid sequence that is complementary to at least one nucleic acid of interest, thereby providing a basis for hybridization and primer extension (see FIG. 1).

In one aspect, one of the universal primers of the universal primer pair is labeled (for example, with a fluorophore) so as to aid downstream applications such as sequencing, genotyping or quantification of second amplification products (second amplicons).

Example 2: Nucleic Acid Amplification Process

The steps necessary for performing an amplification reaction using PCR principles are well known in the art (e.g., denaturation, hybridization, and extension). The instant application provides a method that allows for the amplification of target nucleic acids in a single vessel or single tube and optionally, does not require subsequent addition of enzymes or other amplification components (such as dNTPs or polymerase) other than those present in the initial amplification reaction, prior to completing two rounds of nucleic acid amplification. The method of the instant application reduces the potential for contaminants to enter the reaction mixture and hands on time required to perform the method, making the method suitable to high-throughput processes and/or automation.

The method comprises a multiplex set of TSPPs, a universal primer pair, and reagents necessary for nucleic acid amplification. In a first round of nucleic acid amplification, TSPPs are hybridized to a target nucleic acid of interest using the 3' single-stranded region of the TSPPs as a priming site. The PCR conditions for the first round of nucleic acid amplification include an initial denaturation step (e.g., for example 95° C.), followed by a temperature gradient to reach a first annealing temperature (e.g., 58° C.). Once the first annealing temperature is obtained, the TSPPs and the universal primer pair are present in hairpin configurations. The TSPPs are extended by a polymerase during the extension step (e.g., 72° C.) to form first amplicons while the universal hairpin primers are not. The PCR conditions set forth above are typically repeated several times, so that the low concentration of TSPPs are exhausted prior to, or during, the last cycle of first nucleic acid amplification reaction (see FIG. 2).

Upon completion of the first nucleic acid amplification reaction, the PCR conditions are modified so that the second annealing temperature is raised above the annealing temperature of the first annealing reaction (e.g., between 4° C. and 6° C. higher than the first annealing temperature). By raising the second annealing temperature (for example, 1° C. or 2° C. below, equal to, or 1° C. above, the melting temperature of the universal hairpin primer, the universal primer pair transitions from a hairpin to linear configuration (see FIG. 3). The linear configuration allows the universal primer pair to act as a primer binding site by allowing hybridization to a nucleotide sequence present in the first amplicons (e.g., adaptor sequence). Specifically, the universal primer pair contains a nucleotide sequence that is complementary to the universal adaptor sequence present in the 5' region of the target-specific primers, now part of the first amplicons. After the hybridization step, the universal primer pairs are extended by a polymerase during the second extension step (e.g., 72° C.) to form second amplicons. This set of PCR conditions is typically repeated for about 15 cycles. The second amplicons can then be purified or used in any appropriate downstream application, such as nucleic acid sequencing (see FIG. 4).

Example 3: Microfluidic and Microdroplet Nucleic Acid Amplification Process

In another example, a multiplexed pool of TSPPs, a pair of the fluorescently-labeled universal primers, and target nucleic acids (template) are mixed with reagents necessary for nucleic acid amplification to form a PCR reaction mixture. The PCR reaction mixture can then be partitioned into microdroplets on a microfluidic system (for example as described in U.S. Provisional Patent Applications 61/870, 336, 61/875,312, 61/896,766, 61/905,914, 61/881,040, 61/905,927, 61/934,889, U.S. patent application Ser. No. 14/470,860, and U.S. Pat. No. 9,581,549 each of which is incorporated by reference in their entirety). For example, genomic DNA can be diluted before it is added to the PCR reaction mixture such that only a fraction of a genome will be partitioned into each of the microdroplets formed in the microfluidic system. In one example, genomic DNA is diluted such that on average only a single genomic target will be present in each microdroplet with one or more of the TSPPs. Microdroplets can then be thermally-cycled on the microfluidic system by passing them through thermally controlled zones for PCR. For example, microdroplets can be cycled using a first thermal zone held at a denaturation temperature (for example 97° C. for a period of 15 seconds each cycle), and a second thermal zone held at a first annealing temperature (for example 58° C. for a period of 45 seconds each cycle) for 12 cycles. After the first 12 cycles, the microdroplets can continue cycling through the first thermal (denaturing) zone and a third thermal zone held at a second annealing temperature (for example 62° C. for 45 seconds each cycle) for an additional 38 cycles. In this example, only a single genomic target is present per microdroplet on average, therefore the amplicon generated via PCR will vary in each microdroplet, based on the genomic template present in each of the microdroplets. For example, in a first microdroplet you may have amplification of genetic-target-1, and in a second microdroplet you may have amplification of genetic-target-2, and so on, for the full set of TSPPs. Once the microdroplets complete thermal cycling each microdroplet can be further interrogated with downstream reactions. For example, post-PCR amplification microdroplets can be further injected into new microdroplets through a small orifice and an electric field, as described in U.S. patent application Ser. No. 14/470,860, incorporated herein in its entirety. The newly injected microdroplets can carry a quencher-conjugated nucleic acid designed to hybridize to the fluorophore-conjugated universal hairpin primer. Once the quencher-fluorophore hybrid is formed it can be used for additional sequence interrogation. For example, it can be used to assess the presence of a specific DNA sequence within the PCR amplicon by using a sequence-specific oligonucleotide probe, for example, as described in PCT Publication No. 2012/078710, incorporated herein in its entirety.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of target nucleic acid amplification comprising:
   (1) forming a reaction mixture comprising a first target nucleic acid, a first target primer pair and a universal primer pair:
      (a) the first target primer pair comprising one or two first target-specific hairpin primers, the hairpin primers having
         (i) a 3' target-specific region that is single-stranded at or below a Tm temperature and
         (ii) a 5' region that forms a hairpin below a Tm temperature and that does not form the hairpin above the Tm temperature, wherein the 5' region comprises a universal adaptor sequence, and
      (b) the universal primer pair comprising one or two universal hairpin primers:
         (i) having said 5' region, and
         (ii) lacking said 3' target-specific region;
   (2) annealing in the reaction mixture the 3' single-stranded target-specific region of at least one first target-specific hairpin primer from the first target primer pair to the first target nucleic acid at a temperature at or below the Tm temperature and extending the target-specific hairpin primer with a polymerase in a template-dependent manner to form a first amplicon comprising one or two universal adaptor sequences,
   (3) denaturing the first amplicon into two nucleic acid strands;
   (4) annealing the one or two universal hairpin primers to a universal adaptor sequence of one of the strands of the first amplicon at a temperature above the Tm temperature, and
   (5) extending the one or two universal hairpin primers with a polymerase in a template-dependent manner to form a second amplicon, thereby amplifying the first target nucleic acid.

2. The method of claim 1, wherein the first target primer pair comprises two target-specific hairpin primers or the universal primer pair comprises two universal hairpin primers.

3. The method of claim 1, wherein steps (2) and (3) are repeated multiple times.

4. The method of claim 3, wherein the first target primer pair is exhausted prior to step (4).

5. The method of claim 1, wherein at least one universal hairpin primer is linked to a label such that the label is incorporated into the second amplicon or the first target primer pair is not linked to a label.

6. The method of claim 1, wherein the Tm temperature is at least 2° C. lower than the Tm temperature of the first target-specific hairpin primer.

7. The method of claim 1, wherein the forming further comprises mixing in the reaction mixture a second target primer pair comprising one or two second target-specific hairpin primers, the second target-specific hairpin primers having
   (i) a 3' single-stranded target-specific region different from the 3' single-stranded target-specific region(s) of the first target-specific hairpin primers and
   (ii) said 5' region;
   step (2) comprises annealing at least one second target-specific hairpin primer from the second target primer pair to a second target nucleic acid at a temperature at or below the Tm temperature and extending the second target-specific hairpin primer with the polymerase in a template-dependent manner to form a first extension product comprising one or two universal adaptor sequences,
   step (3) comprises denaturing the first extension product into two nucleic acid strands;
   step (4) comprises annealing the one or two universal hairpin primers to a universal adaptor sequence of one of the strands of the first extension product at a temperature above the Tm temperature, and
   step (5) comprises extending the one or two universal hairpin primers with a polymerase in a template-dependent manner to form a second extension product, thereby amplifying the second target nucleic acid.

8. The method of claim 7, wherein the second target primer pair comprises two target-specific hairpin primers or the one or two universal hairpin primers comprises two universal hairpin primers.

9. The method of claim 7, wherein the forming further comprises mixing in the reaction mixture between 1 and 50 additional target primer pairs, wherein the additional target primer pairs comprise one or two target-specific hairpin primers having: (i) a 3' single-stranded target-specific region that is different from the 3' single-stranded target-specific region of any other target-specific hairpin primer in the mixture, and (ii) said 5' region; and wherein steps (2) through (5) are performed on the first, second, and additional target-specific hairpin primers, thereby amplifying the target nucleic acids.

10. The method of claim 1, wherein the target nucleic acid amplification is performed in a microdroplet.

11. The method of claim 1, wherein the universal hairpin primer pair is at a concentration higher than the target primer pair.

12. The method of claim 11, wherein t the universal hairpin primer pair is at a concentration 1-fold to 10-fold higher than the target primer pair.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Synthetic primer sequence

<400> SEQUENCE: 1
attgcaggcg cctgcaat                                                 18

<210> SEQ ID NO 2
<211> LENGTH: 12
<212> TYPE: DNA
<213> ORGANISM: Artificial Sequence
<220> FEATURE:
<223> OTHER INFORMATION: Synthetic primer sequence

<400> SEQUENCE: 2
aattggccgc ta                                                       12

<210> SEQ ID NO 3
<211> LENGTH: 30
<212> TYPE: DNA
<213> ORGANISM: Artificial Sequence
<220> FEATURE:
<223> OTHER INFORMATION: Synthetic primer sequence

<400> SEQUENCE: 3
attgcaggcg cctgcaataa ttggccgcta                                    30

<210> SEQ ID NO 4
<211> LENGTH: 18
<212> TYPE: DNA
<213> ORGANISM: Artificial Sequence
<220> FEATURE:
<223> OTHER INFORMATION: Synthetic primer sequence

<400> SEQUENCE: 4
attgcaggct taagcaat                                                 18
```